US008003096B2

(12) United States Patent
Carmeliet et al.

(10) Patent No.: US 8,003,096 B2
(45) Date of Patent: Aug. 23, 2011

(54) MEANS AND METHODS FOR THE RECRUITMENT AND IDENTIFICATION OF STEM CELLS

(75) Inventors: Peter Carmeliet, Blanden (BE); Marc Tjwa, Leuven (BE)

(73) Assignees: Vlaams Interuniversitair Instituut voor Biotechnologie VZW, Zwijnaarde (BE); Life Sciences Research Partners VZW, Leuven (BE)

( * ) Notice: Subject to any disclaimer, the term of this patent is extended or adjusted under 35 U.S.C. 154(b) by 1080 days.

(21) Appl. No.: 11/390,931

(22) Filed: Mar. 28, 2006

(65) Prior Publication Data
US 2006/0210532 A1    Sep. 21, 2006

Related U.S. Application Data

(63) Continuation of application No. PCT/EP2004/052432, filed on Oct. 4, 2004.

(30) Foreign Application Priority Data

Oct. 3, 2003 (EP) .................................... 03103675

(51) Int. Cl.
A61K 38/48 (2006.01)
A61K 38/49 (2006.01)
A61K 39/395 (2006.01)
A61K 38/19 (2006.01)
A61K 38/17 (2006.01)
A61K 38/36 (2006.01)

(52) U.S. Cl. ............... 424/94.63; 424/94.64; 424/145.1; 424/130.1; 514/7.7; 514/7.9; 514/8.1; 514/13.5; 514/13.7; 514/14.6; 514/15.3; 514/20.1

(58) Field of Classification Search .................. None
See application file for complete search history.

(56) References Cited

U.S. PATENT DOCUMENTS

| 4,752,603 | A |   | 6/1988  | Collen et al.   |          |
|-----------|---|---|---------|-----------------|----------|
| 4,980,286 | A |   | 12/1990 | Morgan et al.   |          |
| 5,211,947 | A | * | 5/1993  | Brannan et al.  | 424/94.63|
| 5,225,539 | A |   | 7/1993  | Winter          |          |
| 5,840,564 | A |   | 11/1998 | Anderson et al. |          |
| 6,361,946 | B1|   | 3/2002  | Alitalo et al.  |          |
| 6,762,167 | B1| * | 7/2004  | Rodgers et al.  | 424/85.2 |

FOREIGN PATENT DOCUMENTS

| EP | 1 016 413 A1    | 7/2000  |
|----|-----------------|---------|
| WO | WO 92/06180     | 4/1992  |
| WO | WO 92/20316     | 11/1992 |
| WO | WO 92/22635     | 12/1992 |
| WO | WO 93/14188     | 7/1993  |
| WO | WO 93/20221     | 10/1993 |
| WO | WO 00/40260     | 7/2000  |
| WO | WO 2005/032572 A2 | 4/2005 |

OTHER PUBLICATIONS

Hussein et al. (2002) Blood, (Nov. 16, 2002) vol. 100, No. 11,. Abstract No. 1566.*
Cambier et al., Hematology and cell therapy (Apr. 1997) vol. 39, No. 2, pp. 41-48, Abstract Only.*
Stasi et al. (2002) blood 99:1578-1584.*
Kalibala, AIDS Action. Apr. 1990;(10):2-3. Abstract only.*
Gill et al., Leukemia. 1994; 8 Suppl 3:S26-32, Abstract only.*
Lee et al., Am J Physiol. Dec. 1992; 263 (6 Pt 1):G920-6 Abstract only.*
PCT International Search Report, PCT/EP204/052432, dated Jun. 2, 2005.
Ahmed et al., "BDNF Enhances the Differentiation but Not the Survival of CNS Stem Cell-Derived Neuronal Precursors," the Journal of Neuroscience, Aug. 1995, pp. 5765-5778, vol. 15, No. 8.
Broxmeyer et al., "Myelopoietic Enhancing Effects of Murine Macrophage Inflammatory Proteins 1 and 2 on Colony Formation In Vitro by Murine and Human Bone Marrow Granulocyte/Macrophage Progenitor Cells," J. Exp. Med. Nov. 1989, pp. 1583-1594, vol. 170.
Jacobsen et al., "All-Trans- and 9-Cis-Retinoic Acid: Potent and Direct Inhibitors of Primitive Murine Hematopoietic Progenitors In Vitro, " J. Exp. Med., May 1994, pp. 1665-1670, vol. 179.
Swanson et al., "Responses of Hemopoietic Precursors to 13-cis Retinoic Acid and 1 , 25 Dihydroxyvitamin $D_3$ in the Myelodysplastic Syndromes," Blood, Apr. 1986, pp. 1154-1161, vol. 67, No. 4.

* cited by examiner

Primary Examiner — Daniel C Gamett
(74) Attorney, Agent, or Firm — TraskBritt

(57) ABSTRACT

Described are methods of modulating stem/progenitor cell recruitment involving molecules that agonize the formation of plasmin stimulating the recruitment of stem/progenitor cells, including hematopoietic and endothelial precursor cells. Conversely, antagonists of plasmin can inhibit recruitment of the stem cells. In addition, the identification of the uPA receptor (uPAR) as a retention signal for stem cells in their niche suggests a novel method for increased engraftment and isolation of multipotent stem cells.

11 Claims, 7 Drawing Sheets

MEANS AND METHODS FOR THE RECRUITMENT AND IDENTIFICATION OF STEM CELLS

CROSS-REFERENCE TO RELATED APPLICATIONS

This patent application is a continuation of PCT International Patent Application No. PCT/EP2004/052432, filed on Oct. 4, 2004, designating the United States of America, and published, in English, as PCT International Publication No. WO 2005/032572 A2 on Apr. 14, 2005, which application claims priority to European Patent Application No. 03103675.9 filed on Oct. 3, 2003, the contents of the entirety of each of which are incorporated herein by this reference.

TECHNICAL FIELD

The present invention relates generally to biotechnology, and more particularly to new methods of modulating stem cell and/or progenitor cell recruitment.

BACKGROUND

Stem cells include both embryonic and adult stem cells. Adult stems cells include, but are not limited to, hematopoietic stem cells, endothelial stem cells, neural stem cells, muscle stem cells and epithelial stem cells. See Tepper, et al., *Plastic and Reconstructive Surgery*, 111:846-854 (2003). During embryonic and post-natal development, these stem/progenitor cells are located in their respective target organs, where they directly contribute to organogenesis, hematopoiesis, angiogenesis, neurogenesis, etc. In the adult, organs have been formed completely, and multipotent stem/progenitor cells are retained in mitotic quiescence, mostly in the bone marrow (BM), or in target organs (e.g., brain, skeletal and heart muscle, etc.).

In response to physiological stress or injury (e.g., myeloablation, ischemia, etc.), multipotent stem/progenitor cells are mobilized from their quiescent niche under the guidance of chemo- and cytokines, such as SDF1α, G-CSF, VEGF and PlGF.[1-3] Subsequently, they migrate specifically to the damaged organ sites (e.g., hematopoietic, endothelial and epithelial stem cells migrate systemically via blood vessels to sites of tissue ischemia or lung injury; hematopoietic, neural and muscle stem cells migrate locally in the BM, brain and muscle), where they home, integrate and contribute to tissue salvage and regeneration. See Kaushal, et al., *Nat. Med.*, 7:1035-1040 (2001). Conversely, malignant tumor formation, growth and dissemination are caused by expansion and mobilization of so-called cancer stem cells, or supported by mobilized BM-derived (stem/progenitor) cells.

Therefore, a detailed understanding of the molecular mechanisms of retention, proliferation, and recruitment of stem/progenitor cells can result in targeted expansion of the therapeutic armament, both for increased tissue salvage and regeneration, as well as for prevention of cancer growth and dissemination. Hematopoietic and endothelial stem/progenitor cells are retained in the bone marrow (BM) niche via receptor-ligand interactions and mobilized from the BM after proteolytic degradation of these retention complexes, yet the proteinases and retention signals involved remain incompletely identified. It is, however, known that proteases are involved in stem cell mobilization, i.e., up-regulated activity of MMP-9 and neutrophil elastase. These proteases mediate cleavage of anchor molecules (e.g., membrane-bound Kit ligand), thereby liberating quiescent stem/progenitor cells and making them permissive for proliferation and migration. Moreover, BM-derived proteases modulate chemo- and cytokine levels and remodeling of the BM extracellular matrix, resulting in proliferation and migration to the peripheral circulation.[13-14] Conversely, BM-derived proteases also mediate the development and dissemination of malignancy, as neutrophil elastase, taspase and MMPs are implicated in the pathogenesis of leukemia and multiple myeloma. In addition, the identification of the important retention signals involved in keeping the stem/progenitor cells in their quiescent niche, remains incomplete. Several molecules, such as CD26, integrins, CD44, E-selectin, VCAM, etc., have already been identified. However, the identification of novel retention signals is not only important for the development of novel mobilization strategies, but may also improve stem cell isolation, homing and engraftment. The role of the plasmin proteinase system for the mobilization of stem/progenitor cells that reside in the bone marrow remains elusive. However, members of the plasminogen family (e.g., uPA, tPA, uPA receptor (uPAR), plasminogen receptor (Annexin II)) were found to be expressed in the BM, and were associated with leukemia and multiple myeloma.[15-16]

DISCLOSURE OF THE INVENTION

Molecules that agonize the formation of plasmin can stimulate the recruitment of stem/progenitor cells, including hematopoietic and endothelial precursor cells. Conversely, antagonists of plasmin can inhibit recruitment of the stem cells. In addition, the identification of the uPA receptor (uPAR) as a retention signal for stem cells in their niche suggests a novel method for increased engraftment and isolation of multipotent stem cells.

The present invention relates to the role of the plasminogen-plasmin axis in mobilization of bone marrow stem/progenitor cells, more particularly, hematopoietic stem cells and endothelial progenitor cells. Thus, disclosed herein is that, besides the physiological role of plasmin in guarding the delicate balance between coagulation and fibrinolysis, plasmin is also a master switch in mobilization of hematopoietic and endothelial progenitor cells. Hence, molecules capable of increasing plasmin activation or activity can be used for the stimulation of hematopoietic and endothelial progenitor cell mobilization. Conversely, molecules capable of inhibiting plasmin activation or activity can be used for the inhibition of hematopoietic and endothelial progenitor cell mobilization.

In addition, we have found that the uPA receptor (uPAR) is a novel retention signal for quiescent stem/progenitor cells, crucial for adhesion and homing of stem/progenitor cells. This receptor is cleaved during plasmin-mediated mobilization, thereby liberating the stem/progenitor cells from their niche, but the cleaved soluble fragments of uPAR are also endowed with capacity to stimulate stem/progenitor cell mobilization.

DETAILED DESCRIPTION OF THE INVENTION

Figure 1:
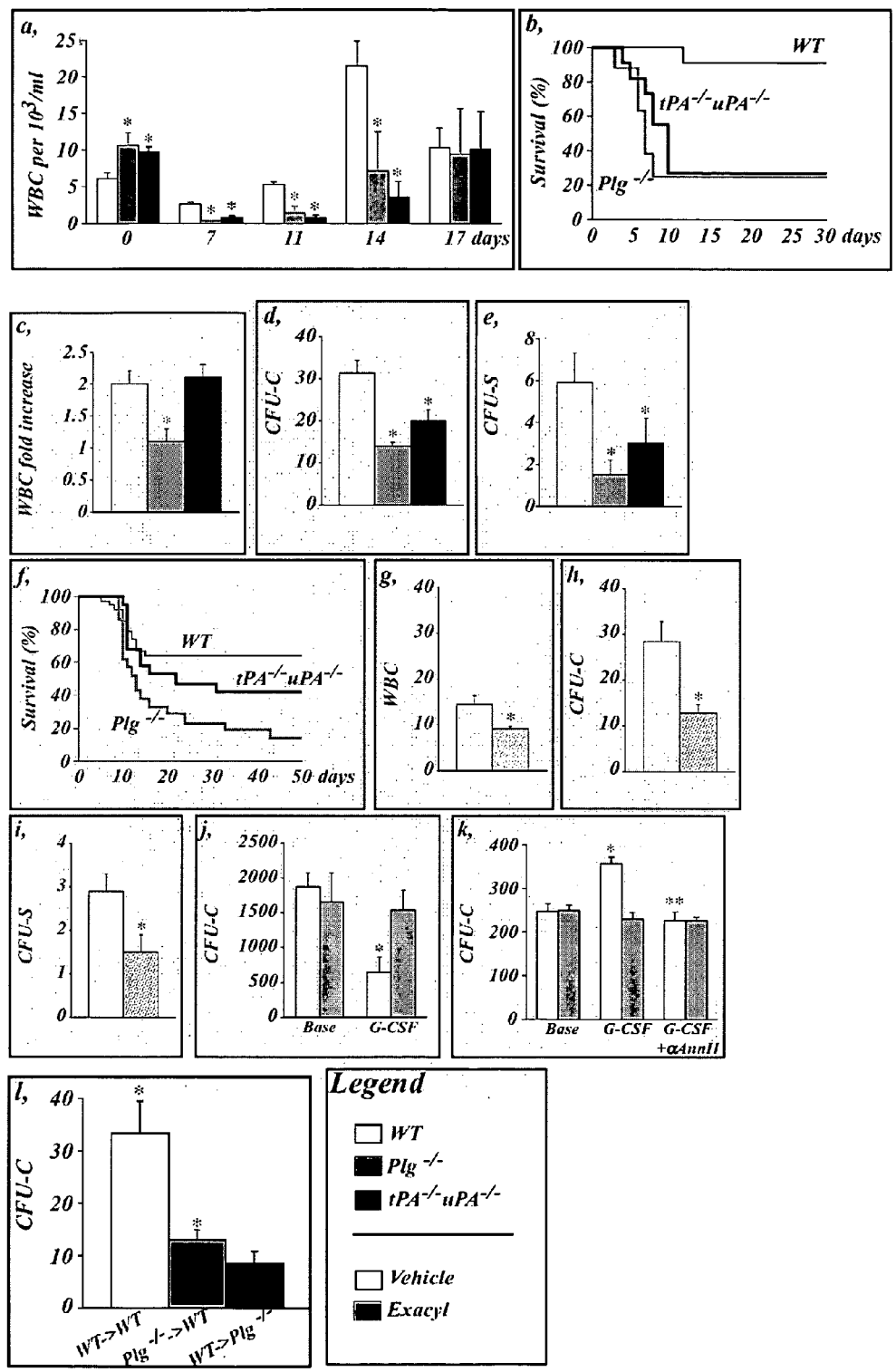
FIG. 1: Deficiency of plasminogen/plasmin results in impaired stem/progenitor cell mobilization. Panels a-b, WT, Plg$^{-/-}$ and tPA$^{-/-}$uPA$^{-/-}$ mice received a single i.v. bolus of 5-FU (200 mg/kg), and were followed up for WBCs (Panel a) and survival (Panel b). *: P<0.05 versus WT; N=8-11. Panels c-f, WT, Plg$^{-/-}$ and tPA$^{-/-}$uPA$^{-/-}$ mice received daily s.c. injections of G-CSF for five days, and circulating WBCs (Panel c), CFU-Cs (Panel d), and CFU-Ss (Panel e) were quantified. *: P<0.05 versus WT; N=8-15. PB MNCs of G-CSF-treated WT, Plg$^{-/-}$ and tPA$^{-/-}$uPA$^{-/-}$ mice were transplanted into lethally irradiated syngeneic WT recipients, and survival was monitored (Panel f). *: P<0.05 versus WT; N=19-39. Panels g-i, WT mice were treated with G-CSF and tranexamic acid or vehicle for five days, and circulating WBCs (Panel g), CFU-Cs (Panel h), and CFU-Ss (Panel i) were quantified. *: P<0.05 versus vehicle; N=10. Panel j, HSCs in the BM of WT and Plg$^{-/-}$ mice in baseline or after G-CSF treatment were quantified after five weeks of culture on AFT024 mouse BM stromal feeder layers. *: P<0.005 versus baseline; N=6. Panel k, CFU-Cs in the BM of WT and Plg$^{-/-}$ mice in baseline or after G-CSF treatment were quantified, without or with pre-incubation with anti-Annexin II antibodies (Santa Cruz Technologies). *: P<0.005 versus baseline; **: P<0.005 versus G-CSF; N=4. Panel l, WT and Plg$^{-/-}$ mice were lethally irradiated and transplanted with BM from syngeneic WT or Plg$^{-/-}$ donor mice. From six weeks after transplantation on, recipient mice had full hematopoietic reconstitution, were treated with G-CSF and circulating CFU-Cs were quantified. *: P<0.005 versus WT≧WT; N=6-9.

Plasmin, a serine protease that circulates in the body as the inactive, proenzyme plasminogen, is involved in the degradation of fibrin clots. Any free circulating plasmin is rapidly inhibited by alpha-2-antiplasmin. Plasminogen binds to both fibrinogen and fibrin, thereby being incorporated into a clot as it is formed. Tissue plasminogen activator (tPA) and, to a lesser degree, urokinase plasminogen activator (uPA) are serine proteases that convert plasminogen to plasmin. Inactive tPA is released from vascular endothelial cells following injury; it binds to fibrin and is consequently activated. Active tPA cleaves plasminogen to plasmin, which then digests the fibrin. Following their release, plasminogen and plasmin are rapidly inactivated by their respective inhibitors. The inhibition of tPA activity results from binding to specific inhibitory proteins. At least four distinct inhibitors have been identified. Of these, plasminogen activator-inhibitors type I and type 2 (PAI-2) are of the greatest physiological significance.

In one embodiment, the present invention relates to the use of plasmin-modulators for the preparation of a medicament to enhance or inhibit the recruitment of stem and/or progenitor cells that reside in the bone marrow. Plasmin modulators can enhance or inhibit the recruitment of bone marrow stem cells and/or bone marrow progenitor cells towards the circulatory blood system. Plasmin modulators can be divided into molecules able to activate (stimulate, enhance) the activity of plasmin and into molecules able to inhibit (antagonize) the activity of plasmin. Accordingly, a molecule able to activate plasmin (stimulates plasmin formation) enhances the recruitment of bone marrow stem cells and/or bone marrow progenitor cells, while a molecule able to inhibit plasmin (inhibits plasmin or inhibits plasmin formation) prevents (inhibits) the recruitment of bone marrow stem cells and/or bone marrow progenitor cells.

First, the activation of plasmin is discussed. The stimulation (enhancement, activation) of the mobilization of stem cells in a mammal is caused by an increase in plasmin or plasmin-like activity in the mammal. Such methods include: the administration of a single composition or a combination of compositions having plasmin or plasmin-like activity, such as plasmin, plasminogen, or chimeric plasminogen; the administration of activators of plasmin, such as tissue-type plasminogen activator (t-PA), a mutant form of t-PA such as tenecteplase, urokinase-type plasminogen activator, alpha-enolase, staphylokinase, streptokinase, or aspirin; the administration of agents able to enhance activator activity or concentration, such as sulodexide, retinoic acid, or microplasmin; peptides able to facilitate active conformation of activators; agents able to stimulate expression of activator genes; the administration of a single agent or a combination of agents able to decrease the activity and/or concentration of inhibitors of plasmin or plasmin activators, such as T-686 ((3E,4E)-3-benzylidene-4-(3,4,5-trimethoxy-benylidene) pyrrolidine-2,5-dione), alpha-2-anti-plasmin inhibitors, or analapril; peptides able to block active conformation of plasminogen inhibitors; and agents able to inhibit expression of plasminogen inhibitor genes.

In the present invention, plasmin-like activity is defined as the ability to cleave a plasmin substrate, such as S-225.

Accordingly, the invention relates to the use of a molecule capable of activating plasmin activity for the manufacture of a medicament to activate bone marrow stem cell and/and or bone marrow progenitor cell mobilization. In a particular embodiment, the stem cell is a hematopoietic stem cell. In another embodiment, the stem cell is an endothelial progenitor cell. In yet another embodiment, the stem cell is a lymphatic endothelial progenitor cell.

In another embodiment, the molecule capable of activating plasmin activity is selected from the list that is chosen from the list comprising plasmin, plasminogen, chimeric plasminogen, tissue-type plasminogen activator, tenecteplase, urokinase-type plasminogen activator, alpha-enolase, staphylokinase, streptokinase, aspirin, sulodexide, retinoic acid, T-686 ((3E,4E)-3-benzylidene-4-(3,4,5-trimethoxy-benzylidene)pyrrolidine-2,5-dione), analapril, an antibody against plasminogen activator inhibitor, an antibody against alpha-2-antiplasmin and microplasmin for the preparation of a medicament to enhance the recruitment of bone marrow stem cells and/or bone marrow progenitor cells.

The wording "to enhance stem cell mobilization" is equivalent with the wording "to enhance stem cell recruitment" and refers to the ability to cause mobilization (recruitment) of stem cells (e.g., from bone marrow into circulation, from the bone marrow into organs such as the lung, kidney, and blood vessels). The enhancement of stem cell mobilization is at least 20%, 30%, 40%, 50%, 60%, 70%, 80%, 90%, 100% or more, when compared to the mammal not receiving the molecule.

A medical diagnosis can identify a subject that suffers from a disease or condition that would benefit from stem cell recruitment. For example, it is known that myelosuppression is a serious side effect of many cancer chemotherapy drugs. Thus, for example, the identifying step comprises selecting a human subject undergoing antineoplastic chemotherapy. The administering of the molecules that activate plasmin to such a subject can be performed before, during, or after a chemotherapy dosing. The administration of molecules that activate plasmin contemporaneously with, or after, administering the antineoplastic chemotherapy is preferred. Similarly, re-establishment of a healthy white blood cell count is critical for bone marrow transplant patients. Thus, in another variation of the embodiment, "identifying" comprises selecting a bone marrow transplant subject as the candidate for receiving molecules that can activate plasmin. A molecule that can activate plasmin is preferably administered contemporaneously with or after the bone marrow transplant. Other diseases that can benefit from an increased stem cell mobilization comprise congenital, cyclic or idiopathic leukopenia or neutropenia, pancytopenia, and AIDS.

In yet another embodiment, non-hematopoietic diseases can also benefit from stimulation or inhibition of mobilization of bone marrow-derived (stem/progenitor) cells through modulation of plasmin activity or activation. It is now amply documented that adult bone marrow-derived progenitor cells can contribute to the revascularization and, thereby, facilitate the regeneration and functional recovery of the ischemic limb and heart (P. Bianco and P. G. Robey, Nature 414:118-21 (2001); A. A. Kocher et al., Nat. Med. 7:430-6 (2001); E. Tateishi-Yuyama et al., Lancet 360:427-35 (2002); B. E. Strauer et al., Circulation 106:1913-8 (2002)). However, the signals that triggered their mobilization remained enigmatic, and there has been a need to identify and characterize such signals and the molecules responsible therefor. Therefore, in yet another embodiment, molecules capable of activation or plasmin activity can be used for the manufacture of a medicament to enhance endothelial progenitor cell mobilization, more specifically, also lymphatic endothelial progenitor cell mobilization. Furthermore, since stimulation of mobilization of bone marrow-derived (stem/progenitor) cells contributes to angiogenesis, tissue regeneration and salvage, enhancement of their mobilization via increasing plasmin activity or activation, it is also envisaged in the present invention to apply plasmin activators for the treatment of ischemic diseases, lung injury, stroke, muscle degeneration or muscle dystrophy, liver injury, kidney injury, etc.

In preferred embodiments, the composition that comprises the molecule able to activate plasmin further comprises a pharmaceutically acceptable carrier.

In a particular embodiment, sulodexide is used for the manufacture of a medicament to activate stem cell mobilization. Sulodexide is a fibrinolytic agent that acts by releasing cellular tissue plasminogen activator. It is currently in use for medical purposes (anti-thrombosis, diabetic nephropathy, etc.). Sulodexide can be administered orally, it has a longer life than plasminogen, and has a reduced effect on global coagulation and bleeding parameters (Harenberg, 1998, *Med. Res. Rev.* 18:1-20). Ampotherin may also be used in the compositions and methods according to the invention. Ampotherin increases the activity of plasminogen and the amount of surface-bound plasmin (Parkkinen, 1993, *J. Biol. Chem.* 268: 19726-19738). Recombinant tPA, or tPA analogs, can also be used in the methods and compositions of the invention (U.S. Pat. No. 4,752,603; U.S. Pat. No. 5,840,564). Furthermore, the use of chimeric plasminogen activators (i.e., a protein comprising at least a biologically active portion of plasminogen activator fused via a peptide bond to a different protein) is also contemplated. An example of such a chimeric plasminogen activator is K2tu-PA (Asselbergs et al., 1995, *J. Biotechnol.* 42(3):221-233). The use of other plasminogen activators, such as uPA, alpha-enolase and gamma-enolase, is also contemplated. It is known that enolase, present on the surface of cells, is capable of binding plasminogen, thereby localizing the plasminogen to the extracellular surface, whereas antibodies against alpha-enolase can be used to inhibit cell surface-mediated plasminogen activation (R. Lopez-Alemany et al. (2003), *Am. J. Hematol.* 72(4):234. The use of saruplase or analogs thereof in the methods and composition of the invention is also contemplated. Saruplase is a recombinant urokinase-type plasminogen activator (White 1998, *J. Am. Coll. Cardiol.* 31:487-496). Plasminogen, streptokinase and urokinase and analogs thereof can also be used in the methods and compositions of the invention. For example, lumbrokinase, which contains plasminogen and plasminogen activator and is currently used for the prevention and treatment of ischemic cerebrovascular disease, may be used according to the invention. It may be given orally in a capsule form. In addition, fragments of plasminogen, streptokinase and urokinases that comprise functional protease domains may also be used. An example of such a fragment is described in Burck et al., 1990, *J. Biol. Chem.* 265:5170-5177, which discloses a fragment of tPA comprising the second kringle and protease domains. The use of agents capable of stimulating the expression and/or release of plasminogen or plasminogen activators is also contemplated (*J. Biol. Chem.* 265:6104-6111, 1990; *Mol. Cell Biol.* 11:3139-3147, 1991). For example, transforming growth factor-beta (TGF-beta) and retinoic acid are able to increase expression of tPA or uPA (Fiumelli et al., 1999, *Eur. J. Neurosci.* 11:1639-1646; Tran et al., 1999, *Stroke* 30:1671-1677; Lansink et al., 1996, *Blood* 88:531-541). It is also possible to increase the expression of the transcription factor Ets-1, which regulates the expression of uPA (Kitange et al., 1999, *Lab. Invest.* 79:407-416). Staphylokinase can also be used in the methods and compositions of the invention. Staphylokinase is a 15 kD bacterial protein that forms a complex with plasmin, which in turn activates other plasminogen molecules by converting them into plasmin (Schlott et al., 1997, *J. Biol. Chem.* 272:6067-6072). The use of aspirin in the compositions and methods of the invention is also contemplated. Aspirin has been reported to stimulate plasmin activity (Milwidsky et al., 1991, *Thrombo. Haemost.* 65:389-393). In a particular embodiment, the use of microplasmin is also contemplated. Microplasmin (developed by ThromboGenics Ltd.) is a low-molecular-mass form of natural plasmin, which fully retains the catalytic potential of the larger parent molecule. In another embodiment, reduction of the activity and/or levels of plasminogen activator inhibitors is also contemplated. For example, plasminogen activator inhibitor 1 (PAI-1) is a serpin that has a key role in fibrin degradation through inhibition of plasminogen activation. Inhibition of PAI-1 can be effected by, for example, the specific inhibitor T-686, (3E,4E)-3-benzylidene-4-(3,4,5-trimethoxy-bezylidene)-pyrrolidine-2,5-dione. Oral administration in mice prevents death by hypercoagulation (Vinogradsky et al., 1997, *Thromb. Res.* 85:305-314). Administration of enalapril also inhibits PAI-1. Sakata et al., 1999, *Am. Heart J.* 137:1094-1099. The use of peptides designed to block the active conformation of PAI-1 or PAI-2 is also contemplated. Sharp, 1999, *Struct. Fold. Res.* 7:111-118; Harrop, 1999, *Struct. Fold. Res.* 7:43-54). Agents capable of reducing the expression of the PAI-I gene, for example, by inhibiting the binding of the promoter element B box that binds the helicase-like transcription factor (HLTF), may also be used in the compositions and methods of the invention (Ding et al., 1999, *J. Biol. Chem.* 274:19573-19580). The use of agents capable of inhibiting the activity of transforming growth factor (TGF)-beta-1 on the activation of the serpin pathway, which pathway blocks plasminogen activation, is also contemplated. An example of such an agent is a TGF-beta neutralizing antibody (Tran et al., 1999, *Stroke* 30:1671-1678).

In a specific embodiment of the present invention, a nucleic acid containing a portion of a gene coding for an inhibitor of plasmin activity, such as PAI-1 or PAI-2, in which inhibitor sequences flank (are both 5' and 3' to) a different gene sequence, is used as a plasmin inhibitor antagonist, or to promote plasmin inhibitor inactivation by homologous recombination (see also, Koller and Smithies, 1989, *Proc. Natl. Acad. Sci. USA* 86:8932-8935; Zijlstra et al., 1989, *Nature* 342:435-438). The nucleic acid sequences of such inhibitors are known to those of skill in the art, and may be found, for example, in a public database such as Genbank. The sequence for PAI-1 has Genbank accession number M16006 (Ginsburg, et al., 1986, *J. Clin. Invest.* 78 (6):1673-1680). The sequence for PAI-2 has Genbank accession number M18082 (Schleuning, et al. 1987, *Mol. Cell. Biol.* 7 (12): 4564-4567). Formulating and administering such nucleic acids can be done with gene therapeutic methods as explained herein further.

A more specific embodiment of the present invention is directed to a method of reducing plasmin inhibitor expression or activity by targeting mRNAs that express the plasmin inhibitor protein. RNA therapeutics currently fall within three classes, antisense species, ribozymes, or RNA aptamers (Good et al., 1997, *Gene Therapy* 4:45-54). Antisense oligonucleotides have been the most widely used. By way of example, but not limitation, antisense oligonucleotide methodology to reduce plasmin inhibitor expression is presented below. Ribozyme therapy involves the administration, induced expression, etc., of small RNA molecules with enzymatic ability to cleave, bind, or otherwise inactivate specific RNAs, to reduce or eliminate expression of particular proteins (Grassi and Marini, 1996, *Annals of Medicine* 28:499-510; Gibson, 1996, *Cancer and Metastasis Reviews* 15:287-299). At present, the design of "hairpin" and "hammerhead" RNA ribozymes is necessary to specifically target a particular mRNA such as that for PAI-1 or PAI-2. RNA aptamers are specific RNA ligand proteins, such as for Tat and Rev RNA (Good et al., 1997, *Gene Therapy* 4:45-54) that can specifically inhibit their translation.

In another embodiment, the activity or levels of a plasmin inhibitor are reduced by administration of an antibody that immunospecifically binds to a plasmin inhibitor, or a fragment or a derivative of the antibody containing the binding domain thereof.

In a specific embodiment, a chimeric antibody is used. Techniques have been developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454) by splicing the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region, for example, humanized antibodies.

In a preferred embodiment, a humanized antibody is used, more preferably an antibody having a variable domain in which the framework regions are from a human antibody and the complementarity-determining regions are from an antibody of a non-human animal, preferably a mouse (see International Patent Application No. PCT/GB8500392 by Neuberger et al. and Celltech Limited).

Complementarity-determining region (CDR) grafting is another method of humanizing antibodies. It involves reshaping murine antibodies in order to transfer full antigen specificity and binding affinity to a human framework (Winter et al. U.S. Pat. No. 5,225,539). CDR-grafted antibodies have been successfully constructed against various antigens, for example, antibodies against IL-2 receptor as described in Queen et al., 1989 (*Proc. Natl. Acad. Sci. USA* 86:10029); antibodies against cell surface receptors-CAMPATH as described in Riechmann et al., 1988 (*Nature* 332:323); antibodies against hepatitis B in Cole et al., 1991 (*Proc. Natl. Acad. Sci. USA* 88:2869); as well as against viral antigens-respiratory syncitial virus in Tempest et al., 1991 (*Bio-Technology* 9:267). CDR-grafted antibodies are generated in which the CDRs of the murine monoclonal antibody are grafted into a human antibody. Following grafting, most antibodies benefit from additional amino acid changes in the framework region to maintain affinity, presumably because framework residues are necessary to maintain CDR conformation, and some framework residues have been demonstrated to be part of the antigen binding site.

However, in order to preserve the framework region so as not to introduce any antigenic site, the sequence is compared with established germline sequences followed by computer modeling.

In other embodiments, fusion proteins of modified immunoglobulins (or functionally active fragments thereof) are used. For example, the modified immunoglobulin may be fused via a covalent bond (e.g., a peptide bond), at either the N-terminus or the C-terminus to an amino acid sequence of another protein (or portion thereof, preferably an at least 10, 20 or 50 amino acid portion of the protein) that is not the modified immunoglobulin. Preferably, the modified immunoglobulin, or fragment thereof, is covalently linked to the other protein at the N-terminus of the constant domain. In preferred embodiments, fusion proteins are used in which the modified immunoglobulin is covalently linked to IL-2, IL-4, IL-5, IL-6, IL-7, IL-10, alpha-interferon, or MHC-derived peptide.

The modified immunoglobulins useful in the methods of the invention include analogs and derivatives that are either modified, i.e., by the covalent attachment of any type of molecule as long as such covalent attachment does not prevent the modified immunoglobulin from generating an anti-idiotypic response. For example, but not by way of limitation, the derivatives and analogs of the modified immunoglobulins include those that have been further modified, for example, by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques including, but not limited to, specific chemical cleavage, acetylation, formylation, metabolic synthesis of tunicamycin, etc. Additionally, the analog or derivative may contain one or more non-classical amino acids.

The subject to be treated by the methods and compositions of the invention is preferably a mammal, most preferably a human, but can also be a non-human animal including, but not limited to, cows, horses, sheep, pigs, fowl (e.g., chickens), goats, cats, dogs, hamsters, mice and rats.

Generally, administration of products of species origin or species reactivity (in the case of antibodies) that is the same species as that of the patient is preferred. Thus, in a preferred embodiment, a human plasmin inhibitor protein, or derivative, homolog or analog thereof; nucleic acids encoding human plasmin inhibitor or a derivative, homolog or analog thereof; or humanized, in the case of antibodies, or other human agents that affect plasmin inhibitor expression or activity, are therapeutically or prophylactically administered in an effective amount to a human patient.

In a specific embodiment of the present invention, a nucleic acid containing a portion of a gene coding for an enhancer of plasmin activity, such as plasminogen, tPA, uPA, alpha- or gamma-enolase is used as a plasmin activity agonist (agonist). A more specific embodiment of the present invention is directed to a method of increasing plasmin activity by expressing mRNAs that code for an enhancer of plasmin activity (Good et al. 1997, *Gene Therapy* 4:45-54).

Generally, administration of products of species origin or species reactivity (in the case of antibodies) that is the same species as that of the patient is preferred. Thus, in a preferred embodiment, a human plasmin activity enhancer protein, or derivative, homolog or analog thereof; nucleic acids encoding a human plasmin activity enhancer or a derivative, homolog or analog thereof, or other human agents that affect plasmin enhancer expression or activity, are therapeutically or prophylactically administered to a human patient.

Preferably, suitable in vitro or in vivo assays are utilized to determine the effect of a specific therapeutic agent and whether its administration is indicated for treatment of the affected tissue or individual. In various specific embodiments, in vitro assays can be carried out with representative cells of cell types involved in a patient's disorder, to determine if a therapeutic agent has a desired effect upon such cell types. The representative cells are preferably bone marrow cells.

In a particular embodiment, it is known that other polypeptide factors that stimulate stem cell recruitment exist, and it is contemplated that such factors will be co-administered with a molecule able to activate plasmin to enhance or modulate the recruitment effects of a molecule able to activate plasmin. In the present invention, we have designated the polypeptide factors that stimulate stem cell recruitment "myelopoietic agents." Myelopoietic agents that can be used in the present invention to stimulate bone marrow stem cell and/or bone marrow progenitor cell recruitment in combination with as hereinabove-described molecules that can activate plasmin comprise G-CSF, M-CSF, GM-CSF, IL-3, SCF, VEGF, VEGF-B, VEGF-C, VEGF-D, PlGF, PDGF-A, PDGF-C, PDGF-D, erythropoietin (EPO) and its functional derivatives and Flt3 ligand. Thus, the method further comprises administering to the subject a myelopoietic agent selected from the group consisting of: (a) granulocyte colony-stimulating factor (G-CSF), macrophage-CSF (M-CSF), granulocyte-macrophage-CSF (GM-CSF), interleukin-3 (IL-3), stem cell factor (SCF), vascular endothelial growth factor (VEGF), vascular endothelial growth factor B (VEGF-B), vascular endothelial growth factor C (VEGF-C), vascular endothelial growth factor D (VEGF-D), placental growth factor (PlGF) platelet-derived growth factor A (PDGF-A), platelet-derived growth factor B (PDGF-B), platelet-derived growth factor C (PDGF-C), and platelet-derived growth factor (PDGF-D); (b) a polynucleotide comprising a nucleotide sequence encoding any member of (a); and (c) combinations of one or more of these polypeptides or polynucleotides. All of these growth factors have been described in literature, including the following: G-CSF Genbank Acc. No. S69115, Shimane et al., "Molecular Cloning and Characterization of G-CSF Induced Gene cDNA," *Biochem. Biophys. Res. Commun.*, 199(1):26-32 (1994); IL-3, Gen Bank Acc. No. M33135, Phillips et al., "Synthesis and expression of the gene encoding human interleukin-3," *Gene*, 84(2):501-507 (1989); M-CSF Genbank Acc. No. M64592, Cerretti et al., "Human Macrophage-Colony Stimulating Factor: Alternative RNA and Protein Processing From a Single Gene," *Mol. Immunol.* 25 (8):761-770 (1988); SCF, Genbank Acc. No. M59964, Martin et al., "Primary Structure and Functional Expression of Rat and Human Stem Cell Factor DNAs," *Cell* 63 (1):203-211 (1990); VEGF clone (a 581 bp cDNA covering bps 57-638, Genbank Acc. No. 15997) VEGF-C cDNA insert (Genbank Acc. No. X94216), see also U.S. Pat. No. 6,361,946; VEGF-D, Gen Bank Acc. No. D89630, Yamada et al., "Molecular Cloning of a Novel Vascular Endothelial Growth Factor, VEGF-D," *Genomics*, 42(3):483-488 (1997); Maglione, et al., *Proc. Natl. Acad. Sci. USA,* 88(20):9267-9271 (1996) (PlGF, GenBank Acc. No. X54936). Granulocyte colony-stimulating factor (G-CSF), Swiss-Priot No. P09919, Nagata et al., "Molecular cloning and expression of cDNA for human granulocyte colony-stimulating factor," *Nature* 319:415-418 (1986); macrophage-CSF (M-CSF), Swiss-Prot No. P09603, Kawasaki et al., "Molecular cloning of a complementary DNA encoding human macrophage-specific colony-stimulating factor (CSF-1)," *Science* 230:291-296 (1985); granulocyte-macrophage-CSF (GM-CSF), Swiss-Prot No.: P04141, Lee et al., "Isolation of cDNA for a human granulocyte-macrophage colony-stimulating factor by functional expression in mammalian cells," *Proc. Natl. Acad. Sci. USA* 82:4360-4364 (1985); interleukin-3 (IL-3), Swiss-Prot No. P26951, Kitamura et al., "Expression cloning of the human IL-3 receptor cDNA reveals a shared beta subunit for the human IL-3 and GM-CSF receptors," *Cell* 66:1165-74 (1991); stem cell factor (SCF), Swiss Prot No: P21583, Martin et al., "Primary structure and functional expression of rat and human stem cell factor DNAs," *Cell* 63:203-211 (1990); vascular endothelial growth factor (VEGF), Swiss Prot No. P15692, Leung et al., "Vascular endothelial growth factor is a secreted angiogenic mitogen," *Science* 246:1306-09 (1989); vascular endothelial growth factor C (VEGF-C), Swiss-Prot No. P49767, Juokov et al., "A novel vascular endothelial growth factor, VEGF-C, is a ligand for the Flt4 (VEGFR-3) and KDR (VEGFR-2) receptor tyrosine kinases," *EMBO. J.* 15:290-298 (1996), *EMBO J.* 15:1751-1751 (1996); vascular endothelial growth factor D (VEGF-D), Swiss-Prot No. O43915, Yamada et al., "Molecular cloning of a novel vascular endothelial growth factor, VEGF-D," *Genomics* 42:483-488 (1997); and placental growth factor (PlGF), Maglione et al., *Proc. Natl. Acad. Sci. USA,* 88(20):9267-71 (1996) (PlGF, GenBank Acc. No. X54936). The subject, or patient, to be treated using the methods of the invention is, for example, a mammal, and is preferably human, and can be a fetus, child, or adult.

Therapeutic agents for use in therapy can be tested in suitable animal model systems prior to testing in humans including, but not limited to, rats, mice, chicken, cows, monkeys, rabbits, etc. For in vivo testing prior to administration to humans, any animal model system known in the art may be used.

In another aspect of using plasmin modulators, the invention can be used in the reverse way and this means that molecules capable of inhibiting plasmin activation can be used for the manufacture of a medicament to inhibit bone marrow stem cell and/or bone marrow progenitor cell mobilization. The molecules capable of inhibiting plasmin activation are selected from the list comprising: PAI-1, PAI-2, alpha-2 anti-plasmin, an antibody against u-PA, an antibody against plasminogen, an antibody against plasmin, an antibody against alpha-enolase, an antibody against the plasminogen receptor annexin II, tranexanic acid. Still other molecules capable of inhibiting plasmin activation comprise specific anti-tPA antibodies (e.g., against different epitopes of the human tPA protein (Holvoet et al., *Eur J Biochem* 1986, 158:173-77), such as, for example, the active site of t-PA), tPA-stop which are commercially available small peptides (available through American Diagnostica), binding to different sites of t-PA (Pawlak et al. (2002) *Neuroscience* 113(4): 995-1001; Neuhoff et al. (1999) *Eur. J. of Neurosc.* 1999, 11:4241-50), mutant PAI protein, e.g., that only binds to plasminogen activators, available at American Diagnostica), or virus-mediated overexpression (Kirkegaard et al. (1999) *Eur. J. Biochem.* 263:577-86; Nicole et al. (2001) *Nat. Med.* 7:59-64). In a specific embodiment, the bone marrow stem cells are hematopoietic stem cells. In yet another specific embodiment, the bone marrow stem cells are endothelial progenitor cells. In yet another specific embodiment, the bone marrow stem cells are lymphatic endothelial progenitor cells.

Thus, the suppression (inhibition) of bone marrow cell and/or bone marrow progenitor cell mobilization is obtained by the addition of plasmin inhibitors to a subject. Diseases that thus benefit from anti-plasmin therapy through a suppression of bone marrow stem cell and/or bone marrow progenitor cell mobilization, comprise myeloproliferative diseases, leukemias, myelodysplastic disorders, myelofibrosis, polycytemia vera, Hodgkin lymphoma and non-Hodgkin lymphoma, essential thrombocytosis and multiple myeloma. Second, since solid non-hematopoietic tumors also depend on the recruitment of, and interaction with, bone marrow-derived (stem/progenitor) cells, suppression of their mobilization via inhibiting plasmin activity or activation is also possible with the present invention.

In a specific embodiment, plasmin inhibitors can be used in combination with chemotherapeutics for the manufacture of a medicament to treat hematopoietic and non-hematopoietic tumors.

In the following section, gene therapeutic methods are herein further explained. Nucleic acids comprising a sequence encoding a plasmin activity enhancer, such as plasmin, plasminogen, tPA, uPA, alpha-enolase or gamma-enolase, or a functional derivative thereof, are administered to enhance plasmin activity by way of gene therapy. Gene therapy refers to therapy performed by the administration of a nucleic acid to a subject. In this embodiment of the present invention, the nucleic acid expresses its encoded protein(s) that mediates a therapeutic effect by modulating plasmin activity. Any of the methods for gene therapy available in the art can be used according to the present invention. Exemplary methods are described below.

The nucleic acid sequences of the above proteins are known to those of skill in the art and may be found, for example, in a public database such as Genbank. The sequence for PAI-1 has Genbank accession number M16006 (Ginsburg et al., 1986, *J. Clin. Invest.* 78(6):1673-1680). The sequence for PAI-2 has Genbank accession number M18082 (Schleuning et al., 1987, *Mol. Cell. Biol.* 7(12):4564-4567). The sequence for tPA has Genbank accession number M15518 (Harris et al., 1986, *Mol. Biol. Med.* 3(3):279-292). The sequence for uPA has Genbank accession number M115476 (Holmes et al., 1985, *Biotechnology* (N.Y.) 3:923-929. The sequence for alpha-enolase has Genbank accession number M22349 M27833 (Oliva et al., 1989, *Gene* 79(2):355-360). The sequence for gamma-enolase has Genbank accession number M14328 (Giallongo et al., 1986, *Proc. Natl. Acad. Sci.* 83(18):6741-6745).

For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; Morgan and Anderson, 1993, *Ann. Rev. Biochem.* 62:191-217; and May, 1993, *TIBTECH* 11:155-215. Methods commonly known in the art of recombinant DNA technology that can be used are described in Ausubel et al., eds., 1993, *Current Protocols in Molecular Biology*, John Wiley & Sons, NY; and Kriegler, 1990, *Gene Transfer and Expression, A Laboratory Manual*, Stockton Press, NY. In a preferred aspect, the therapeutic agent comprises a nucleic acid coding for an enhancer of plasmin activity that is part of an expression vector that expresses the enhancer of plasmin activity. In particular, such a nucleic acid has a promoter operably linked to the plasmin activity enhancer coding region, the promoter being inducible or constitutive, and optionally, tissue-specific, preferably brain-specific or neuron-specific. Plasmin inhibitor function may be inhibited by use of antisense nucleic acids. The present invention provides the therapeutic or prophylactic use of nucleic acids of at least six nucleotides and are preferably oligonucleotides (ranging from 6 to about 200 oligonucleotides) that are antisense to a gene or cDNA encoding a plasmin inhibitor, or portions thereof. A "plasmin inhibitor 'antisense' nucleic acid" as used herein refers to a nucleic acid capable of hybridizing to a portion of a plasmin inhibitor nucleic acid (preferably mRNA) by virtue of some sequence complementarity. The antisense nucleic acid may be complementary to a coding and/or noncoding region of a plasmin inhibitor mAw. In specific aspects, the oligonucleotide is at least six nucleotides, at least ten nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at any position (examples of such modifications can be found in: Bailey, *Ullmann's Encyclopedia of Industrial Chemistry* (1998), 6th ed. Wiley and Sons). Such antisense nucleic acids have utility in inhibiting plasmin inhibitor function or activity and can be used for the manufacture of a medicament to enhance the mobilization of stem cells.

The plasmin inhibitor antisense nucleic acids can be directly administered to a cell, or can be produced intracellularly by transcription of exogenous, introduced sequences. Alternatively, plasmin inhibitor antisense nucleic acids are produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector can remain episomal or become chromosomally integrated, as long as it can be transcribed to produce the desired antisense RNA. Such vectors can be constructed by recombinant DNA technology methods standard in the art.

The antisense nucleic acids of the invention comprise a sequence complementary to at least a portion of an RNA transcript of a plasmin inhibitor gene, preferably a human plasmin inhibitor gene. However, absolute complementarity, although preferred, is not required.

The amount of plasmin inhibitor antisense nucleic acid that will be effective in the treatment of a particular disorder or condition will depend on the nature of the disorder or condition, and can be determined by standard clinical techniques. Where possible, it is desirable to determine the antisense cytotoxicity in vitro, and then in useful animal model systems prior to testing and use in humans.

In a specific embodiment, pharmaceutical compositions comprising plasmin inhibitor antisense nucleic acids are administered via liposomes, microparticles, or microcapsules. In various embodiments of the invention, it may be useful to use such compositions to achieve sustained release of the plasmin inhibitor antisense nucleic acids.

In a specific embodiment, it may be desirable to utilize liposomes targeted via antibodies to specific identifiable central nervous system cell types (Leonetti et al., 1990, *Proc. Natl. Acad. Sci. USA* 87:2448-2451; Renneisen et al., 1990, *J. Biol. Chem.* 265:16337-16342).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, for example, by constructing it as part of an appropriate nucleic acid expression vector and administering it so that it becomes intracellular, for example, by infection using defective or attenuated retroviral or other viral vector (U.S. Pat. No. 4,980,286), or by direct injection of naked DNA, or by use of microparticle bombardment (e.g., a gene gun; Biolistic, Dupont), or coating with lipids or cell-surface receptors, or through use of transfecting agents, by encapsulation in liposomes, microparticles, or microcapsules, or by administering it in linkage to a peptide that is known to enter the nucleus, or by administering it in linkage to a ligand subject to receptor-mediated endocytosis that can be used to target cell types specifically expressing the receptors (e.g., Wu and Wu, 1987, *J. Biol. Chem.* 262:4429-4432), etc.

In another embodiment, a nucleic acid-ligand complex can be formed in which the ligand comprises a fusogenic viral peptide that disrupts endosomes, allowing the nucleic acid to avoid lysosomal degradation.

In yet another embodiment, the nucleic acid can be targeted in vivo for cell-specific uptake and expression, by targeting a specific receptor (see, for example, International Patent Publications WO 92/06180, WO 92/22635, WO 92/20316, WO 93/14188 and WO 93/20221).

In a specific embodiment, a viral vector that contains the plasmin activity enhancer-encoding nucleic acid is used. In another specific embodiment, a viral vector that contains an inhibitor of plasmin activity antisense nucleic acid is used. For example, a retroviral vector can be used (Miller et al., 1993, *Meth. Enzymol.* 217:581-599). These retroviral vectors have been modified to delete retroviral sequences that are not necessary for packaging of the viral genome and integration into host cell DNA. The coding or antisense nucleic acids to be used in gene therapy is/are cloned into the vector, which facilitates delivery of the gene into a patient. More detail about retroviral vectors can be found in Boesen et al., 1994, *Biotherapy* 6:291-302, which describes the use of a retroviral vector to deliver the mdr1 gene to hematopoietic stem cells in order to make the stem cells more resistant to chemotherapy. Other references illustrating the use of retroviral vectors in gene therapy are Clowes et al., 1994, *J. Clin. Invest.* 93:644-651; Kiem et al., 1994, *Blood* 83:1467-1473; Salmons and Gunzberg, 1993, *Human Gene Therapy* 4:129-141; and Grossman and Wilson, 1993, *Curr. Opin. in Genetics and Devel.* 3:110-114. Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are the liver, the central nervous system, endothelial cells (such as prostate cells) and muscle. Adenoviruses have the advantage of being capable of infecting non-dividing cells (Kozarsky and Wilson, 1993, *Current Opinion in Genetics and Development* 3:499-503, discuss adenovirus-based gene therapy). The use of adenovirus vectors to transfer genes to the respiratory epithelia of rhesus monkeys has been demonstrated by Bout et al., 1994, *Human Gene Therapy* 5:3-10. Other instances of the use of adenoviruses in gene therapy can be found in Rosenfeld et al., 1991, *Science* 252:431-434; Rosenfeld et al., 1992, *Cell* 68:143-155; and Mastrangeli et al., 1993, *J. Clin. Invest.* 91:225-234. Adeno-associated virus (AAV) has also been proposed for use in gene therapy (Walsh et al., 1993, *Proc. Soc. Exp. Biol. Med.* 204:289-300).

Another approach to gene therapy involves transferring a gene into cells in tissue culture by methods such as electroporation, lipofection, calcium phosphate-mediated transfection, or viral infection. Usually, the method of transfer includes the transfer of a selectable marker to the cells. The cells are then placed under selection to isolate those cells that have taken up and are expressing the transferred gene from these that have not. Those cells are then delivered to a patient. In this embodiment, the nucleic acid is introduced into a cell prior to administration in vivo of the resulting recombinant cell. Such introduction can be carried out by any method known in the art including, but not limited to, transfection by electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, for example, Loeffler and Behr, 1993, *Meth. Enzymol.* 217: 599-618; Cohen et al., 1993, *Meth. Enzymol.* 217:618-644; Cline, 1985, *Pharmac. Ther.* 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably, is heritable and expressible by its cell progeny.

The resulting recombinant cells can be delivered to a patient by various methods known in the art. In a preferred embodiment, cells are injected, for example, into the spinal cord, heart, and/or brain. Recombinant blood cells (e.g., hematopoietic stem or progenitor cells) are preferably administered intravenously. The number of cells envisioned for use depends on the desired effect, patient state, etc., and can be determined by one skilled in the art. Cells into which a nucleic acid can be introduced for purposes of gene therapy encompass any desired, available cell type and include, but are not limited to, epithelial cells, endothelial cells, keratinocytes, neuronal cells, hippocampal cells, fibroblasts, muscle cells, hepatocytes, blood cells such as T lymphocytes, B lymphocytes, monocytes, macrophages, neutrophils, eosinophils, megakaryocytes, and granulocytes, various stem or progenitor cells, in particular hematopoietic stem or progenitor cells, for example, as obtained from bone marrow, umbilical cord blood, peripheral blood, fetal liver, etc.

In a preferred embodiment, the cell used for gene therapy is autologous to the patient.

In one embodiment in which recombinant cells are used in gene therapy, a plasmin activity enhancer encoding nucleic acid is introduced into the cells such that the gene is expressible by the cells or their progeny, and the recombinant cells are then administered in vivo for therapeutic effect. In a specific embodiment, stem or progenitor cells are used, such as, for example, hematopoietic stem cells or endothelial progenitor cells. With respect to hematopoietic stem cells (HSCs), any technique that provides for the isolation, propagation, and maintenance in vitro of HSCs can be used in this embodiment of the invention. Techniques by which this may be accomplished include (a) the isolation and establishment of HSC cultures from bone marrow cells isolated from the future host or a donor, or (b) the use of previously established long-term HSC cultures, which may be allogeneic or xenogeneic. Non-autologous HSCs are used preferably in conjunction with a method of suppressing transplantation immune reactions between the future host and patient. In a particular embodiment of the present invention, human bone marrow cells can be obtained from the posterior iliac crest by needle aspiration (see, for example, Kodo et al., 1984, *J. Clin. Invest.* 73:1377-1384). In a preferred embodiment of the present invention, the HSCs can be made highly enriched or in substantially pure form. This enrichment can be accomplished before, during, or after long-term culturing, and can be done by any technique known in the art. Long-term cultures of bone marrow cells can be established and maintained by using, for example, modified Dexter cell culture techniques (Dexter et al., 1977, *J. Cell Physiol.* 91:335) or Witlock-Witte culture techniques (Witlock and Witte, 1982, *Proc. Natl. Acad. Sci. USA* 79:3608-3612).

In a specific embodiment, the nucleic acid to be introduced for purposes of gene therapy comprises an inducible promoter operably linked to the coding or antisense region, such that expression of the nucleic acid is controllable by controlling the presence or absence of the appropriate inducer of transcription.

The following section gives an overview of the pharmaceutical compositions, which can be used in combination with activators or inhibitors of plasmin activation. The pharmaceutical compositions according to the present invention preferably comprise one or more pharmaceutically acceptable carriers and the active constituents (thus, activators or inhibitors of plasmin activation). The carrier(s) must be "acceptable" in the sense of being compatible with the other ingredients of the composition and not deleterious to the recipient thereof. In a preferred embodiment, the active ingredient of the pharmaceutical composition according to the present invention is purified. In specific embodiments, the active ingredient is a protein, and is purified to be 50%, 75%, 90%, 95% or 99% pure protein by weight. It will be appreciated that the amounts of the active constituents required for the manufacture of a medicament to modulate stem cell mobilization will vary according to the route of administration, the condition, age, and file history of the subject, and the galenic formulation of the pharmaceutical composition, etc.

The actually administered amounts of active constituents may be decided by a supervising physician; however, an effective amount to treat disorders described herein depends on the usual factors such as the nature and severity of the disorders being treated and the weight of the mammal. A unit dose will normally contain 0.01 to 50 mg, for example, 0.01 to 10 mg, or 0.05 to 2 mg of plasmin modulators (an activator or an inhibitor) or a pharmaceutically acceptable salt thereof. Unit doses will normally be administered continuously or once or more than once a day, for example, two, three, or four times a day, more usually one to three times a day, such that the total daily dose is normally in the range of 0.0001 to 1 mg/kg; thus a suitable total daily dose for a 70 kg adult is 0.01 to 50 mg, for example, 0.01 to 10 mg or more usually, 0.05 to 10 mg. Therapeutic formulations include those suitable for parenteral (including intramuscular and intravenous), oral, rectal, intrathecal or intradermal administration, although oral administration is the preferred route. Thus, the pharmaceutical composition may be formulated as tablets, pills, syrups, capsules, suppositories, formulations for transdermal application, powders, especially lyophilized powders for reconstitution with a carrier for intravenous administration, etc. The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring. Therapeutic formulations suitable for oral administration, for example, tablets and pills, may be obtained by compression or molding, optionally with one or more accessory ingredients. Compressed tablets may be prepared by compressing one or more active constituents in a suitable apparatus into tablets having a suitable size. Prior to the mixing, the one or more active constituents may be mixed with a binder, a lubricant, an inert diluent and/or a disintegrating agent, a diluent, a lubricant and/or a surfactant.

In a preferred embodiment, one or more active constituents are mixed with a binder, such as microcrystalline cellulose, until a homogeneous mixture is obtained.

Subsequently, another binder, such as polyvidone, is transferred to the mixture under stirring. This mixture is passed through granulating sieves and dried by desiccation before compression into tablets in a standard compressing apparatus.

A tablet may be coated or uncoated. An uncoated tablet may be scored. A coated tablet may be coated with sugar, shellac, film or other enteric coating agents.

Therapeutic formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising one or more active constituents that is to be reconstituted by dissolving in a pharmaceutically acceptable carrier that dissolves one or more active constituents, for example, an aqueous solution of carboxymethylcellulose and lauryl sulfate.

When the pharmaceutical composition is a capsule, it may contain a liquid carrier, such as a fatty oil, for example, cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides.

In yet another embodiment, the therapeutic compound can be delivered in a controlled release system. In one embodiment, a pump may be used (see Langer, supra; Sefton, *CRC Crit. Ref. Biomed. Eng.* 14:201(1987); Buchwald et al., *Surgery* 88:507 (1980); Saudek et al., *N. Engl. J. Med.* 321:574 (1989). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.* 23:61 (1983); see also Levy et al., *Science* 228: 190 (1985); During et al., *Ann. Neurol.* 25:351 (1989); Howard et al., *J. Neurosurg.* 71:105 (1989)).

In yet another embodiment, a controlled release system can be placed in proximity of the therapeutic target, i.e., the spinal cord, the brain, or the heart, thus requiring only a fraction of the systemic dose (see, for example, Goodson, in *Medical Applications of Controlled Release*, supra, vol. 2, pp. 115-138 (1984)). Other controlled release systems are discussed in the review by Langer (*Science* 249:1527-1533 (1990)).

In one embodiment of the pharmaceutical composition according to the invention, two or more active constituents are comprised as separate entities. The two entities may be administered simultaneously or sequentially.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In a particular embodiment, plasmin activators, such as native or recombinant t-PA, is administered by intravenous (i.v.) injection. The invention also provides a pharmaceutical pack or kit comprising one or more sterile syringes and containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

It is now amply documented that adult bone marrow-derived progenitor cells can contribute to the revascularization and, thereby, facilitate the regeneration and functional recovery of the ischemic limb and heart (P. Bianco and P. G. Robey, Nature 414:118-21 (2001); A. A. Kocher et al., Nat. Med. 7:430-6 (2001); E. Tateishi-Yuyama et al., Lancet 360:427-35 (2002); B. E. Strauer et al., Circulation 106:1913-8. (2002)); however, the signals that trigger their mobilization remain more enigmatic, and there is a need to identify and characterize such signals and the molecules responsible therefor. Therefore, in yet another embodiment, molecules capable of activation plasmin activity can be used for the manufacture of a medicament to enhance endothelial progenitor cell mobilization, more specifically, also lymphatic endothelial progenitor cell mobilization.

In preferred embodiments, the composition that comprises the molecule able to activate plasmin further comprises a pharmaceutically acceptable carrier.

In yet another embodiment, the proteolytically cleaved targets of plasmin can also be used for the manufacture of a medicament to stimulate stem cell mobilization. We have shown that one target is the urokinase receptor (uPAR). Hence soluble uPAR (suPAR) is used for the manufacture of a medicament to stimulate stem cell mobilization. In a particular embodiment, soluble uPAR is used for bone marrow and/or endothelial progenitor stem cell mobilization. In yet another particular embodiment, soluble uPAR is used for hematopoietic stem cell mobilization. In yet another particular embodiment, soluble uPAR is used for endothelial progenitor cell mobilization. In yet another particular embodiment, soluble uPAR is used for lymphatic endothelial progenitor cell mobilization.

In yet another embodiment, the stimulation of stem cell mobilization with soluble uPAR can be carried out ex vivo. Thus, a biological sample from a mammalian subject, wherein the sample comprises stem cells, and contacting the stem cells with soluble uPAR or a functional fragment thereof. In this method, the beneficial effects of soluble uPAR are imparted to cells from a human or animal subject outside of the body of the human or other animal subject. Such therapy may be desirable to prepare a treated cell sample for use in a medical procedure. The biological sample can be any tissue or fluid sample from which stem cells are found. Blood and bone marrow are preferred sources for the biological sample, as is umbilical cord blood.

In a preferred embodiment, the biological sample is subjected to at least some purification and/or isolation procedures to purify or isolate the stem cells. For example, removal of red blood cells from a blood sample constitutes one level of purification/isolation. Still further purification, for example, to select those nucleated cells that are CD34+ and/or VEGFR-1+, may be performed prior to the treatment with a molecule able to activate plasmin. In a preferred embodiment, the purified stem cells comprise VEGFR-1+ or CD34+ or CD133+ stem cells. Still more preferred, are stem cells that comprise two or more of these markers. Likewise, in some variations of the invention, it is desirable to purify or isolate the stem cells after treatment with a soluble uPAR, to select those cells that have proliferated in response to the molecule. In one variation, the contacting step comprises culturing the stem cells in a culture containing soluble uPAR. In preferred variations, the method further comprises a step of returning the stem cells to the mammalian subject from which they were originally removed. Alternatively, the method comprises a step of transplanting the cells into a different mammalian subject. Human subjects are preferred. In preferred embodiments, the cell donor is a close relative or has a substantially identical human leukocyte antigen (HLA) profile. Such ex vivo therapy is useful in a variety of contexts. For example, with a human subject that needs antineoplastic chemotherapy, healthy stem cells can be removed prior to the chemotherapy, cultured according to the invention, and returned following the chemotherapy. Thus, the biological sample is obtained prior to administering a dose of chemotherapy and the stem cells are returned to the human subject after the contacting step and after the dose of chemotherapy. The method also is useful for autologous or heterologous bone marrow transplantation. Similarly, the stem cells treated according to the method of the invention are expected to improve the success and reduce side effects of organ or tissue transplantation and graft attachments. In one variation, the cells are seeded into a tissue, organ, or artificial matrix ex vivo, and the tissue, organ, or artificial matrix is attached, implanted, or transplanted into the mammalian subject.

In a specific embodiment, hematopoietic stem/progenitor cell transplantation is used in the treatment of many hematological disorders, for example, leukemia and myelodysplastic syndromes, whereas stem cell-based therapy holds can also be used to treat a variety of non-hematological diseases, for example, ischemic disorders, neurodegenerative diseases and diabetes. However, many limitations preclude optimal clinical application, such as obtaining sufficient yields of engrafting and purified populations of stem cells. With regard to hematological transplantations, current markers do not specifically identify engrafting stem cells (e.g., CD34) (Bhatia et al. (1998) Nat. Med. 4:1038-45; H. Nakauchi (1998) Nat. Med. 4:1009-10; Kuci et al. (2003) Blood 101:869-76), or result in limited and non-transplantable yields (e.g., AC133). As the availability of immuno-compatible bone marrow (BM) donors is sparse, the yields of engrafting stem/progenitor cells out of alternative donor sources (e.g., cord blood) are currently only sufficient for pediatric transplantations (Christopherson II et al. (2004) Science 305:1000-3), and attempts for ex vivo expansion of stem cells for clinical transplantation have been disappointing so far. Therefore, advances in transplantation with limited numbers of stem/progenitor cells can only be realized when efficiency of isolation, homing and engraftment of transplantable stem/progenitor cells to BM niches is increased (Christopherson II et al. (2004) Science 305:1000-3). Although several receptors, such as CD26, integrins, CD44, E-selectin, VCAM, Tie-2, etc., have been implicated in the homing and retention of stem/progenitor cells in the BM niche, the identification of novel retention signals is heavily warranted. Moreover, the capacity to isolate more "pure" and better engrafting stem cell populations also benefit non-hematological stem/progenitor transplantation strategies for, e.g., ischemic disorders, neurodegenerative diseases and diabetes.

In the present invention, we have identified the uPA receptor (uPAR) as a receptor being present on stem cells and endothelial progenitor cells. In this regard, the present invention envisages the use of uPAR (e.g., via an antibody with a specificity for uPAR in combination with magnetic beads sorting (MACS sorting) or with fluorescent-activated cell sorting (FACS sorting)) as a marker to enrich stem cell populations. Accordingly, the present invention provides methods of isolating mammalian stem cells expressing uPAR. These methods involve binding a population of cells to a molecule that specifically binds uPAR and isolating the cells that bind to the molecule. The molecule specifically binding to uPAR can be an antibody, a ligand, a peptide, a DNA, a small molecule, or any other suitable molecule. In one specific embodiment, the molecule specifically binding to uPAR is an antibody. In another embodiment, after the stem cells have been isolated, the stem cells can be further enriched, i.e., purified by additional rounds of isolation using positive markers characteristic of stem cells (e.g., CD34 and/or AC133 and/or VEGFR-1 and/or Sca-1) and/or negative markers (e.g., CD38 and/or Lin). In another embodiment, after the stem cells have been isolated by positive markers characteristic of stem cells (e.g., CD34 and/or AC133 and/or VEGFR-1 and/or Sca-1) and/or negative markers (e.g., CD38 and/or Lin), the stem cells can be further enriched, i.e., purified by additional rounds of isolation using uPAR as positive marker. There are many potential sources for the purification of stem cells. For example, embryonic cells are collected from fetal tissue and adult stem cells are derived from mature tissue. Examples of adult stem cells include liver cells that proliferate following partial hepatectomy, hematopoietic cells that can reconstitute the blood following lethal irradiation or chemotherapy, satellite cells that repair damaged skeletal muscle, keratinocyte precursors that participate in wound healing and neural precursor cells involved in brain repair. Thus, the population of cells can be from an embryonic mammal, or from the postnatal mammal, including fetal liver, umbilical cord blood, a yolk sac of the mammal, a mature spinal cord, bone marrow, or an adult peripheral blood sample. The cells can also be from the central nervous system, including the meninges. Preferably, the isolated stem cells of the present invention are hematopoietic stem cells and/or endothelial progenitor cells. The resulting compositions of stem cells can be administered to a mammal for prophylactic and/or therapeutic treatments of various conditions. Treatments of the conditions can involve induction of hematopoiesis, vasculogenesis and/or angiogenesis, myogenesis, liver regeneration and/or neurogenesis.

Therapeutic and Medical Uses of the Present Invention:

The present invention shows that the plasminogen-plasmin proteinase system is a crucial check-point for the mobilization of bone marrow (BM)-derived leukocytes and stem/progenitor cells and, therefore, constitutes an attractive novel therapeutic target for both the stimulation as well as the inhibition of their mobilization. First, as current mobilization strategies for peripheral stem cell transplantations are sometimes endowed with adverse side-effects and poor responders, mobilization is improved via plasmin activators described hereinbefore that increase plasmin activity/activation or represent plasmin-targets (e.g., suPAR). Second, as BM transplantation and chemotherapeutical strategies are associated with severe myeloablation and immunocompromised conditions, rapid restoration of normal hematopoiesis via compounds described hereinbefore, which increase plasmin activity/activation or represent plasmin-targets (e.g., suPAR), is an attractive novel strategy to shorten the deleterious nadir period. Third, as the contribution of BM-derived leukocytes and stem/progenitor cells in tissue salvage and regeneration of blood vessels, heart, muscle, brain, lung, kidney, etc., is increasingly acknowledged, enhanced stem/progenitor cell mobilization via compounds described hereinbefore, which increase plasmin activity/activation or represent plasmin-targets (e.g., suPAR), is attractive for a wide spectrum of pathological conditions (e.g., tissue ischemia). Fourth, the inhibition of BM-derived stem/progenitor cell mobilization via compounds, which inhibit plasmin activity/activation or plasmin-targets (e.g., suPAR), constitutes an attractive novel targeted anti-cancer strategy. Fifth, the inhibition of BM-derived leukocyte mobilization via agents described hereinbefore, which inhibit plasmin activity/activation or plasmin-targets (e.g., suPAR), constitutes an attractive novel targeted anti-inflammation strategy. In addition, evaluation of the plasmin proteinase system in stem/progenitor cell mobilization has identified a novel retention signal for stem cells, i.e., the uPA receptor uPAR. As research on the biology of stem/progenitor cells and their therapeutic application are hampered by the lack of specific immunophenotypical stem cell markers, positive selection based on expression of uPAR (e.g., via magnetic beads or FACS sorting) not only enriches cell populations for stem cells, but also enhances functional homing and engraftment after transplantation in vivo. Finally, the crucial role of the plasmin proteinase system in mobilization of BM-derived stem/progenitor cells has diagnostic implications as well. As early identification of poor responders optimizes mobilization treatment and stem cell transplantation, (genetic) pre-screening for members of the plasmin proteinase system is a novel diagnostic target. In addition, the pivotal role for the plasminogen/plasmin proteinase system in the BM warrants further investigations for a possible pathogenic role in myeloproliferative diseases, including leukemia and lymphoma. These investigations not only result in increased understanding of the above-mentioned diseases, but also in novel means for early diagnosis and targeted therapies.

The invention is further described with the aid of the following illustrative examples.

EXAMPLES

1. Loss or Inhibition of Plasmin Reduces Stem/Progenitor Cell Mobilization

To study the role of the plasminogen proteinase system with its plasminogen activators tPA and uPA, and active plasmin in stem/progenitor cell mobilization, mice lacking plasminogen ($Plg^{-/-}$), tPA ($tPA^{-/-}$), uPA ($uPA^{-/-}$) and both activators ($tPA^{-/-}uPA^{-/-}$) were used.[17, 18] Age- and sex-matched mice were kept in IVC cages. Mobilization was induced either via a single sublethal injection i.v. of the myeloablative agent 5-fluorouracil (5-FU, 200-250 mg/kg), or via administration s.c. of recombinant human G-CSF (Filgrastim, Amgen, 200 µg/kg/d) for five consecutive days.[12] Peripheral blood (PB) samples were obtained by retro-orbital bleeding under light anesthesia. Full blood counts were determined on the Abbott Cell Dyn 1300 hemocytometer. The number of mobilized hematopoietic progenitor cells (HPCs) in the circulation was determined via methylcellulose-based CFU-C assays (MethoCult, Stem Cell Technologies), per $10^5$ peripheral blood mononuclear cells (PB MNCs).[12] The number of mobilized hematopoietic stem cells (HSCs) in the circulation was quantified via splenic colony-forming assays (CFU-S), and evaluated for long-term engraftment via transplantation into lethally irradiated syngeneic wild-type recipients (9.5 Gy total body irradiation). Evaluation of baseline hematopoietic cell counts in transgenic animals showed no gross abnormalities compared to wild-type (WT) mice, as previously documented.[17, 18] We found that a single i.v. bolus of 5-FU in WT mice elevated plasmin activity in BM plasma five-fold above baseline (chromogenic assay: 75±14 U after 5-FU versus 14±2 U in control; N=4; P=0.034). Administration of a sublethal dose of 5-FU to WT mice induced BM depletion and a drop in white blood cell (WBC, FIG. 1, Panel a), red blood cell (RBC) and platelet counts, from which the mice recovered after 2.5 to 3 weeks. Only 10% of WT mice did not survive this dose of 5-FU, succumbing around day 12. In contrast, up to 75% of the $Plg^{-/-}$ or $tPA^{-/-}uPA^{-/-}$ mice died, usually already after six days (FIG. 1, Panel b), and recovery of WBCs (FIG. 1, Panel a), RBCs and platelets was significantly delayed. Analysis of the BM also revealed a significant delay in the recovery of myeloid, lymphoid and megakaryocyte lineages after 5-FU in $Plg^{-/-}$ mice. $Gr1^{+CD}11b^{+}$ myeloid cell counts at day 7 after 5-FU were 29±13 in WT mice and only 3±2 in $Plg^{-/-}$ mice ($\times 10^4$ per femur, N=3; P<0.05), whereas $CD3\epsilon^{+}$ lymphoid cell counts at day 7 after 5-FU were 438±122 in WT mice versus 67±31 in $Plg^{-/-}$ mice ($\times 10^4$ per femur, N=3; P<0.05). By H&E and VWF staining, fewer megakaryocytes, identified as large cells with lobulated nuclei and basophilic staining, were present in 5-FU-treated $Plg^{-/-}$ mice compared to WT mice. Moreover, at seven days after 5-FU, plasmin deficiency reduced the number of BM HSCs ($Sca-1^{+}cKit^{+}$ cells$\times 10^4$ per femur: 42±9 in WT mice versus 5±1 in $Plg^{-/-}$ mice; N=3; P<0.05) and HPCs ($Sca-1^{+}$ cells$\times 10^4$ per femur: 206±20 in WT mice versus 48±22 in $Plg^{-/-}$ mice; N=3; P<0.05). Thus, plasmin proteolysis is required for tri-lineage hematopoietic recovery and mobilization following 5-FU.

The role of plasmin proteolysis in stem cell mobilization in response to five daily injections of recombinant G-CSF was also evaluated. G-CSF treatment in WT mice increased the number of circulating WBCs, HPCs and HSCs in the peripheral blood (FIG. 1, Panels c-e). In contrast, $Plg^{-/-}$ or $tPA^{-/-}uPA^{-/-}$ mice failed to respond to G-CSF treatment (FIG. 1, Panels c-e). To evaluate whether plasmin mobilized HSCs capable of reconstituting hematopoiesis, peripheral blood mononuclear cells (PB-MNCs) from G-CSF-treated mice were transplanted in lethally irradiated WT recipients. Transplantation of PB-MNCs from $Plg^{-/-}$ or $tPA^{-/-}uPA^{-/-}$ mice resulted in significantly reduced survival (FIG. 1, Panel f). In addition, pharmacological inhibition of plasmin by tranexamic acid (exacyl) suppressed stem/progenitor cell mobilization. Compared to control vehicle, administration of exacyl to WT mice reduced G-CSF-induced mobilization of WBCs, HPCs and HSCs by 37%, 55% and 49%, respectively (FIG. 1, Panels g-i). Thus, plasmin proteolysis is also required for G-CSF-driven mobilization.

2. Loss of Plasminogen/Plasmin Reduces HSC Translocation and HPC Expansion

As it is known in the art that translocation and expansion of the stem/progenitor cell pool precedes their mobilization (Heissig et al. (2002), *Cell* 109:625-37; (Drize et al. (1996), *Exp Hematol* 24:816-22), we investigated whether the impaired stem/progenitor cell mobilization in the absence of plasminogen was due to defective stem cell expansion. In steady state, the number of HSCs and HPCs in the BM of $Plg^{-/-}$ mice was comparable to WT mice (FIG. 1, Panels j and k). G-CSF treatment in WT mice reduced the number of HSCs by 65%, and increased the number of HPCs by 44% in the bone marrow after two days (FIG. 1, Panels j and k). In contrast, HSC translocation and HPC expansion in the bone marrow was completely abolished in G-CSF-treated $Plg^{-/-}$ mice (FIG. 1, Panels j and k). Furthermore, the BM proliferation index (i.e., number of proliferating BM cells in G-CSF-treated mice, expressed as percent of proliferating BM cells in control mice) significantly increased in WT but not in $Plg^{-/-}$ mice (167±14% in WT mice versus 73±8% in $Plg^{-/-}$ mice; N=8; P<0.0001). Furthermore, 5-FU treatment induced significantly fewer cycling stem cells in $Plg^{-/-}$ than WT mice ($Sca-1^{+}$ progenitors in S-phase of the cell cycle ($\times 10^4$ per femur): 8.4±0.8 in WT mice versus 1.2±0.6 in $Plg^{-/-}$ mice; N=3; P=0.007). Thus, plasminogen is required for stem/progenitor cell expansion during mobilization.

To further delineate the role of plasminogen/plasmin, we performed BM transplantation experiments, as described previously (Heymans et al. (1999) *Nat. Med.* 5:1135-42), to specifically ablate plasminogen expression in the microenvironment or hematopoietic cells, respectively. Plasminogen was expressed in the interstitial fluid of the murine BM (BM plasma: 810±124 ng/ml; N=3) and in BM-derived hematopoietic cells (BM cell extracts: 53±3 ng/mg protein; N=3). Transplantation of WT BM did not restore G-CSF-mediated mobilization in $Plg^{-/-}$ mice, suggesting that host-derived plasminogen is required, presumably via conversion to plasmin (FIG. 1, Panel l). Surprisingly, transplantation of Plg-deficient BM blunted G-CSF-mediated mobilization in WT mice (FIG. 1, Panel l). However, G-CSF did not increase the pericellular proteolytic capacity of BM cells, suggesting a non-proteolytic role for plasminogen. As antibody-mediated functional inhibition of the plasminogen receptor Annexin II abolished HPC expansion in G-CSF-treated WT but not $Plg^{-/-}$ mice (FIG. 1k), and Annexin II was expressed by murine BM-derived stem cells, BM cell-derived plasminogen may modulate stem/progenitor cell expansion, presumably via autocrine binding to its receptor Annexin II.

Figure 2:
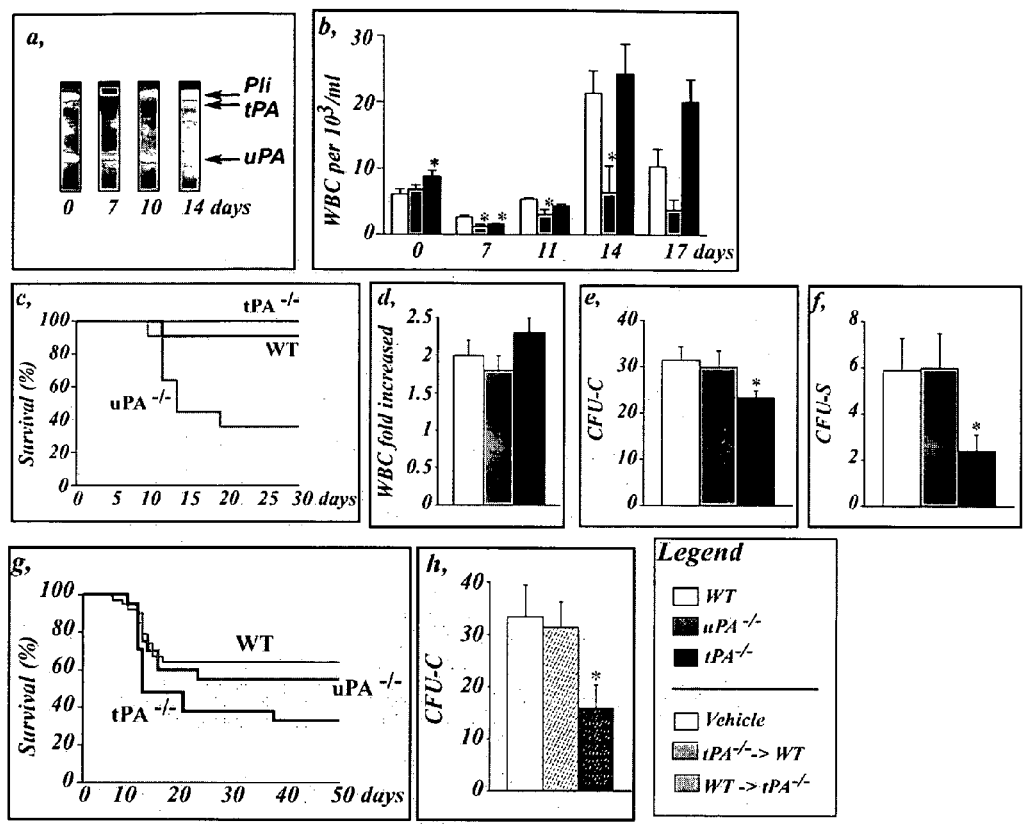
FIG. 2: uPA versus tPA in stem/progenitor cell mobilization. Panel a, representative casein zymography on BM plasma samples of WT mice in baseline or after 5-FU treatment, showing increased uPA activity. Panels b and c, WT, uPA$^{-/-}$ and tPA$^{-/-}$ mice received a single i.v. bolus of 5-FU (200 mg/kg), and were followed up for WBCs (b) and survival (c). *: P<0.05 versus WT; N=11-12. Panels d-g, WT, uPA$^{-/-}$ and tPA$^{-/-}$ mice received daily s.c. injections of G-CSF for five days, and circulating WBCs (Panel d), CFU-Cs (Panel e), and CFU-Ss (Panel f) were quantified. *: P<0.05 versus WT; N=9-15. PB MNCs of G-CSF-treated WT, uPA$^{-/-}$ and tPA$^{-/-}$ mice were transplanted into lethally irradiated syngeneic WT recipients, and survival was monitored (Panel g). *: P<0.05 versus WT; N=20-39. Panel h, WT and tPA$^{-/-}$ mice were lethally irradiated and transplanted with BM from syngeneic WT or tPA$^{-/-}$ donor mice. From six weeks after transplantation on, when normal hematopoiesis was restored, recipient mice were treated with G-CSF and circulating CFU-Cs were quantified. *: P<0.05 versus WT≧WT; N=5-6.

3. Loss of uPA or tPA Differentially Reduces Stem/Progenitor Cell Mobilization Casein zymography on BM plasma of WT mice revealed that levels of active uPA, but not tPA, increased following 5-FU (FIG. 2, Panel a). Compared to WT or $tPA^{-/-}$ mice, $uPA^{-/-}$ mice had increased mortality and delayed hematopoietic recovery (FIG. 2, Panels b and c). In the BM, uPA deficiency resulted in delayed recovery of myeloid and lymphoid lineages, as evaluated by FACS analysis. Moreover, uPA deficiency reduced the number of BM HSCs ($Sca1^{+}cKit^{+}$) and HPCs ($Sca1^{+}$) after 5-FU. Thus, uPA is the responsible plasminogen activator, generating plasmin during 5-FU-induced stem cell mobilization. After G-CSF treatment, the levels of active tPA, but not uPA, increased in the BM plasma, when measured by casein zymography. Furthermore, in vitro clot lysis, expressed as a percentage of a positive standard, was greater when using BM plasma samples from G-CSF-treated WT than $tPA^{-/-}$ mice, confirming that tPA levels were up-regulated in response to G-CSF (79±2% in WT mice versus 58±2% in $tPA^{-/-}$ mice; N=4; P=0.001). To assess whether the specific up-regulation of tPA in response to G-CSF was functionally relevant, we determined whether $tPA^{-/-}$ mice were capable of mobilizing stem/progenitor cells in response to G-CSF. Consistent with the specific up-regulation of tPA, G-CSF-induced mobilization of stem/progenitor cells was impaired in $tPA^{-/-}$ but not in $uPA^{-/-}$ mice (FIG. 2, Panels d-g). In addition, survival of lethally irradiated WT recipients was significantly reduced when transplanted with PB-MNCs from G-CSF-treated $tPA^{-/-}$ mice (FIG. 2, Panel g). Moreover, when WT mice were lethally irradiated and transplanted with $tPA^{-/-}$ BM, stem/progenitor cells were mobilized normally in response to G-CSF (FIG. 2, Panel h). In contrast, mobilization of stem/progenitor cells was impaired when $tPA^{-/-}$ mice were transplanted with WT BM (FIG. 2, Panel h). As only stem/progenitor cells, but not endothelial or stromal cells, engraft in the bone marrow microenvironment after bone marrow transplantation (Simmons et al. (1987), *Nature* 328:429-32; Lennon et al. (1986), *Exp. Hematol.* 14:287-92; Laver et al.

(1987), Blood 70:1966-8), these findings suggest that expression of tPA by stromal and endothelial cells, but not by the repopulating stem/progenitor, was critical. Thus, tPA drives plasmin activity during G-CSF-induced stem cell mobilization.

Figure 3:
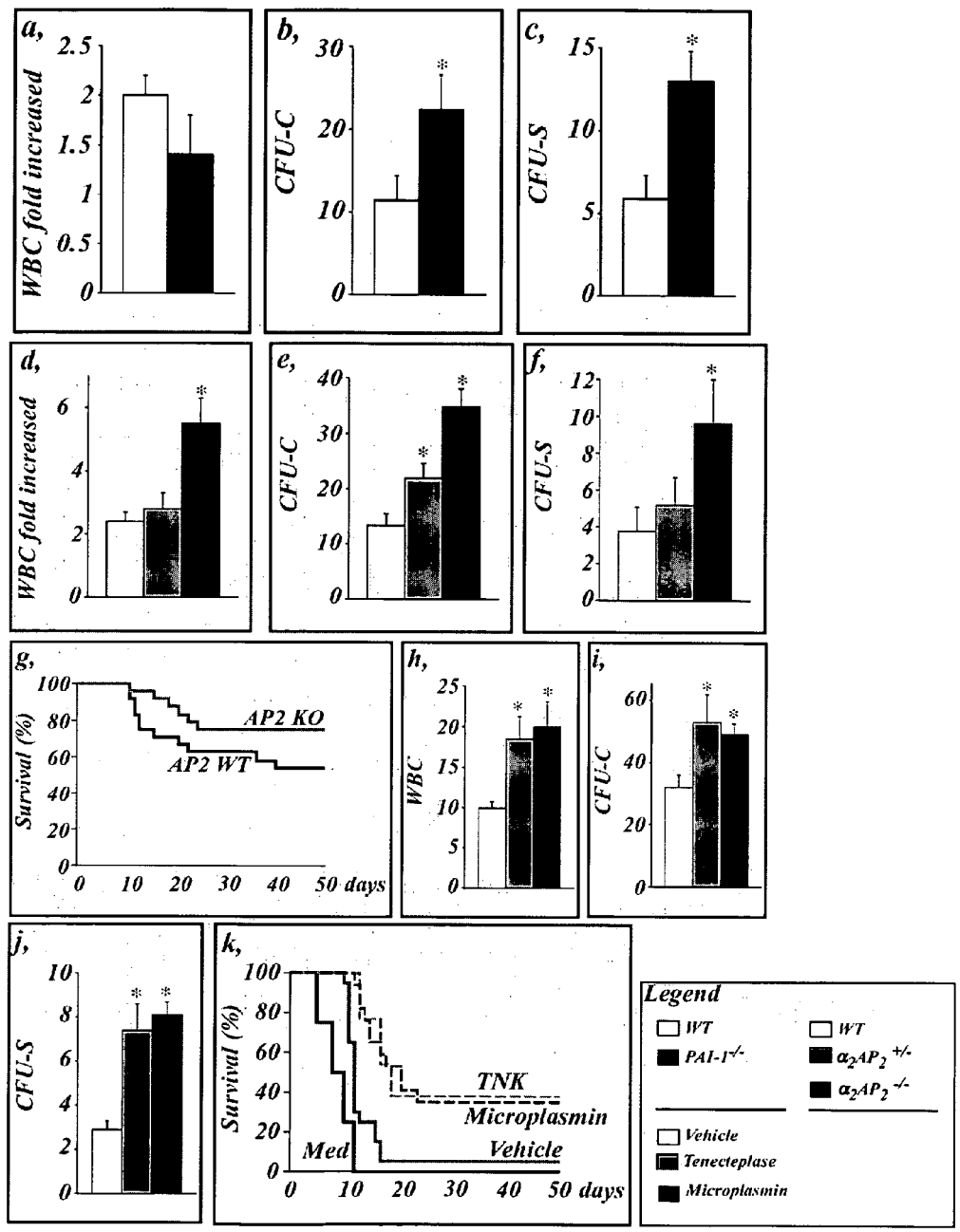
FIG. 3: Loss of plasmin inhibitors and administration of fibrinolytics stimulates stem/progenitor mobilization. Panels a-c, WT and PAI-1$^{-/-}$ mice received daily s.c. injections of G-CSF for five days, and circulating WBCs (Panel a), CFU-Cs (Panel b), and CFU-Ss (Panel c) were quantified. *: P<0.05 versus WT; N=10-15. Panels d-g, WT $\alpha_2$-AP$^{+/-}$ mice and $\alpha_2$-AP$^{-/-}$ mice received daily s.c. injections of G-CSF for five days, and circulating WBCs (Panel d), CFU-Cs (Panel e), and CFU-Ss (Panel f) were quantified. *: P<0.05 versus WT; N=10. PB MNCs from treated WT and $\alpha_2$-AP$^{-/-}$ mice were transplanted into lethally irradiated syngeneic WT recipients, and survival was monitored (Panel g). *: P<0.05 versus vehicle; N=24. Panels h-k, WT received daily s.c. injections of G-CSF in conjunction with treatment of vehicle, 100 mg/kg tenecteplase (daily i.p.) or 100 μg/day microplasmin (osmotic minipump) for five days, and circulating WBCs (Panel h), CFU-Cs (Panel i), and CFU-Ss (Panel j) were quantified. *: P<0.05 versus vehicle; N=10-15. PB MNCs from treated WT mice were transplanted into lethally irradiated syngeneic WT recipients, and survival was monitored (Panel k). As control group, lethally irradiated WT mice were injected with medium only. *: P<0.05 versus vehicle; N=13-20.

4. Enhanced G-CSF-Induced Stem/Progenitor Cell Mobilization in PAI-1$^{-/-}$ and $\alpha_2$AP$^{-/-}$ Mice To extend our findings that tPA/plasmin promoted stem cell mobilization in response to G-CSF, we analyzed mice lacking PAI-1 (PAI-1$^{-/-}$) or $\alpha_2$-antiplasmin ($\alpha_2$AP$^{\pm}$; $\alpha_2$AP$^{-/-}$), the primary inhibitors of tPA and plasmin, respectively. In response to G-CSF, PAI-1$^{-/-}$ mice mobilized more stem and progenitor cells in the peripheral blood (FIG. 3a-c). In addition, $\alpha_2$AP deficiency increased, in a gene dose-dependent manner, G-CSF-driven mobilization of WBCs, HPCs and HSCs (FIG. 3d-j). Furthermore, when lethally irradiated WT mice were transplanted with PB-MNCs, survival of these recipients was increased when PB-MNCS were used from $\alpha_2$AP$^{-/-}$ donors (FIG. 3g). Thus, genetic deficiency of plasmin inhibitors improved G-CSF-mediated stem/progenitor cell mobilization.

5. Administration of Fibrinolytica Enhances G-CSF-Induced Stem Cell Mobilization Our genetic and pharmacological findings that stem cell mobilization was suppressed by reduced tPA and plasmin levels, while enhanced by elevated tPA and plasmin levels (due to loss of the inhibitors) prompted us to evaluate whether administration of fibrinolytica to WT mice could stimulate stem cell mobilization. The latter can be therapeutically attractive for patients, who are refractory or poorly respond to G-CSF (Cottler-Fox et al. (2003) Hematology (Am Soc Hematol Educ Program) 419-37). Compared to G-CSF alone, administration of G-CSF in combination with recombinant tPA variant tenecteplase (TNK), a well-know fibrinolytic agent used for daily hospital treatment of acute cardio- and cerebrovascular syndromes (Collen D (2001) Hematology (Am Soc Hematol Educ Program 1-9), clearly enhanced mobilization of WBCs, HPCs and HSCs in WT mice by 87%, 65%, and 155%, respectively (FIG. 3h-f). HSCs, mobilized by G-CSF and TNK, were functional, as transplantation of these cells significantly increased the survival of lethally irradiated WT recipient mice (FIG. 3k). Because of bleeding diathesis, novel fibrinolytica with increased safety profile are being developed such as recombinant human microplasmin (µPli), which is a plasmin variant lacking the five kringle domains, and increases fibrinolysis via inhibiting $\alpha_2$AP activity (Nagai et al. (2003) J Thromb Haemost 1:307-13). Combinatory treatment of G-CSF and microplasmin enhanced mobilization of WBCs, HPCs and functional HSCs in WT mice by 102%, 52%, and 179%, respectively (FIG. 3h-k). Moreover, µPli co-administration was associated with merely mild bleeding diathesis, as previously documented (Suzuki et al. (2004) J Thromb Haemost 2:1617-21). Thus, increasing plasmin activity is a novel and alternative therapeutic strategy for stem cell mobilization.

6. Patients Treated with Thrombolytica Show Increased Stem Cell Mobilization We have shown that increasing plasmin activity synergized G-CSF-mediated mobilization in mice. In a next step, we examined whether the use of fibrinolytica in humans can also induce stem/progenitor cell mobilization. For this, peripheral blood samples before and 24 hours after thrombolytic treatment (staphylokinase or tenecteplase) were collected from patients admitted at the Coronary Care Unit (University Hospital Gasthuisberg, Leuven, Belgium) with acute myocardial infarction, and were evaluated for circulating numbers of HSCs and HPCs, using FACS analysis (CD34$^+$) and methylcellulose culture assays, respectively. At time of admission (i.e., before onset of treatment), the number of mobilized CD34$^+$ HSCs and HPCs was minimal (CFU-C per 10$^6$ MNCs: 19±10; N=5). Following thrombolytic treatment, the number of circulating CFU-Cs and CD34$^+$ stem/progenitor cells increased four-fold (CFU-C per 10$^6$ MNCs: 83±44; N=5; P=0.145). Thus, increased plasmin activity clearly amplifies mobilization of BM-derived stem/progenitor cells in patients.

7. Loss of tPA Reduces Endothelial Progenitor Cell Mobilization

Ischemia is characterized by the rapid restoration of tissue perfusion, both via local proliferation of vascular cells, as well as via the recruitment of BM-derived (stem/progenitor) cells (P. Carmeliet (2003), Nat. Med. 9:653-60). As ischemia rapidly up-regulates the expression of chemo- and cytokines (De Falco et al. (2004), Blood DOI 10.11182/blood-2003-12-4423), and cytokine-mediated stem/progenitor cell mobilization was highly dependent on tPA activity, we investigated whether tPA was involved in ischemia-driven stem/progenitor cell mobilization. For this, we ligated the right femoral artery in WT and tPA$^{-/-}$ mice as previously described (Luttun et al. (2002), Nat. Med. 8:831-40), and evaluated mobilization of endothelial progenitor cells (EPCs) via the spleen late-outgrowth EPC assay and quantified using staining for isolectin-B4 and incorporation of acetylated-LDL (Dimmeler et al. (2001), J. Clin. Invest. 108:391-7). Late-outgrowth EPC had abundant expression of tPA (copies per copy β-actin: 368±268; N=3). In steady state, EPC mobilization was minimal in WT mice (EPCs/mm$^2$: 664±102; N=5). Upon ligation, EPC mobilization was significantly up-regulated (EPCs/mm$^2$: 2031±490; N=5; P<0.05). In contrast, preliminary data show that ischemia-driven mobilization of EPCs is attenuated in ligated tPA$^{-/-}$ mice.

8. Increasing Plasmin Activity Stimulates Ischemia-Driven Stem/Progenitor Cell Mobilization As increased plasmin activity via genetic loss of plasmin inhibitors or administration of fibrinolytica significantly amplified cytokine-mediated stem/progenitor cell mobilization, we are investigating whether genetic loss of plasmin inhibitors or administration of fibrinolytica stimulates ischemia-driven stem/progenitor cell mobilization and post-ischemic revascularization. First, WT and $\alpha_2$-AP$^{-/-}$ mice, or WT mice treated with fibrinolytica are subjected to limb ischemia, and EPC mobilization and revascularization (i.e., morphology, perfusion and functional recovery) are quantified, as described previously (Luttun et al. (2002), Nat. Med. 8:831-40). Second, WT and $\alpha_2$-AP$^{-/-}$ mice are transplanted with BM from syngeneic WT and $\alpha_2$-AP$^{-/-}$ mice, transgenically overexpressing GFP. These transplanted mice have labeled BM cells, which allow us to trace down mobilized BM-derived stem/progenitor cells. We observe that EPC mobilization and functional recovery is increased in ligated $\alpha_2$-AP$^{-/-}$ mice compared to WT mice.

Figure 4:
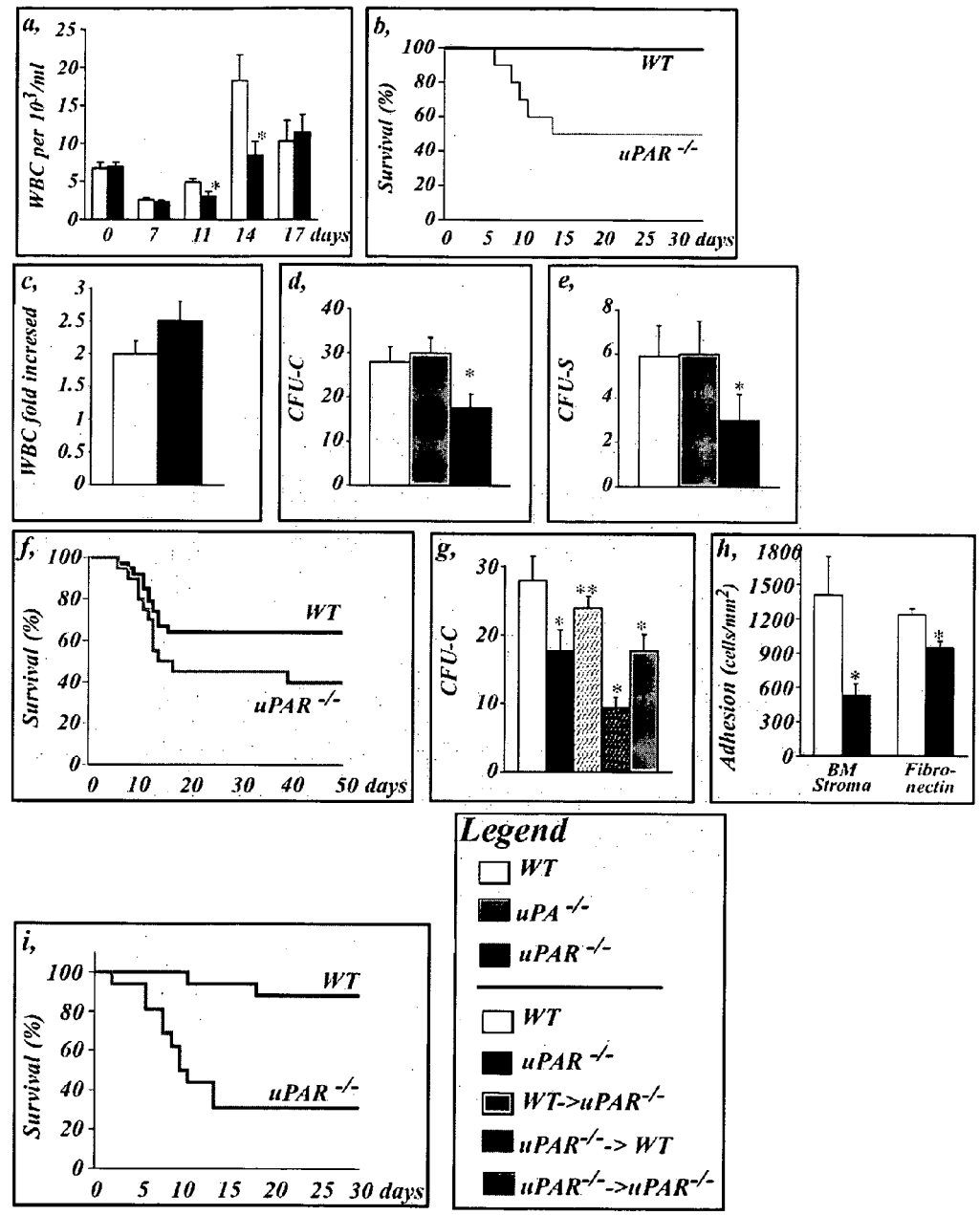
FIG. 4: Plasmin-mediated bone marrow matrix remodeling, and uPAR is required for HSC/HPC mobilization and retention. Panels a-b, WT and uPAR$^{-/-}$ mice received a single i.v. bolus of 5-FU (250 mg/kg), and were followed up for WBCs (Panel a) and survival (Panel b). *: P<0.05 versus WT; N=11. Panels c-f, WT and uPAR$^{-/-}$ mice received daily s.c. injections of G-CSF for five days, and circulating WBCs (Panel c), CFU-Cs (Panel d), and CFU-Ss (Panel e) were quantified. *: P<0.05 versus WT; N=11-15. PB MNCs of G-CSF-treated WT and uPAR$^{-/-}$ mice were transplanted into lethally irradiated syngeneic WT recipients, and survival was monitored (Panel g). *: P<0.05 versus WT; N=20-39. Panel g, critical role of uPAR on donor cells for mobilization. WT and uPAR$^{-/-}$ mice were lethally irradiated and transplanted with BM from syngeneic WT or uPAR$^{-/-}$ donor mice. From six weeks after transplantation on, when normal hematopoiesis was restored, recipient mice were treated with G-CSF and circulating CFU-Cs were quantified. *: P<0.05 versus WT; **: P<0.05 versus uPAR$^{-/-}$; N=8-9. Panel h, adhesion of BM MNCs onto BM stromal cells or fibronectin was impaired in the absence of uPAR. *: P<0.05 versus WT; N=5. Panel i, crucial role of uPAR on donor cells for long-term engraftment. Lethally irradiated splenectomized WT mice were transplanted with low numbers of WT or uPAR$^{-/-}$ BM cells and survival was monitored.

9. The uPA Receptor (uPAR) is Crucial for Stem/Progenitor Cell Homing and Retention We also studied the role of the uPA receptor uPAR, which localizes uPA to the cell surface and increases peri-cellular plasmin proteolysis. Consistent with a role of uPA in stem cell mobilization in response to 5-FU, stem cell recruitment was also defective in uPAR$^{-/-}$ mice after 5-FU-induced myeloablation, and resulted in reduced survival (FIG. 4, Panels a and b). As uPA was not involved in stem cell mobilization in response to G-CSF, we had expected that loss of uPAR would not affect G-CSF-induced recruitment. However, mobilization of stem/progenitor cells in response to G-CSF was also impaired in uPAR$^{-/-}$ mice (FIG. 4, Panels c-f), suggesting that uPAR might have a role in stem cell mobilization, independent of uPA. In addition, BM transplantation experiments revealed that transplantation of WT BM in uPAR$^{-/-}$ mice rescued the impaired mobilization, whereas WT mice transplanted with uPAR$^{-/-}$ BM failed to mobilize their stem cells efficiently (FIG. 4, Panel g). These findings not only indicate that uPAR has a role in stem cell mobilization, but they also suggest that uPAR is present on engrafting stem cells. Indeed, FACS analysis indicated that murine Sca1$^+$ BM-derived stem/progenitor cells expressed uPAR. As uPAR mediates $\beta_1$-integrin-mediated leukocyte adhesion (Blasi et al. (2002), *Nat. Rev. Mol. Cell Biol.* 3:932-43; Plesner et al. (1997), *Stem Cells* 15:398-408; Tarui et al. (2001), *J. Biol. Chem.* 276: 3983-90), we examined whether uPAR was involved in stem/progenitor cell adhesion. Compared to WT, fewer uPAR$^{-/-}$ BM MNCs indeed adhered to stromal or onto fibronectin (FIG. 4, Panel h). Moreover, when splenectomized WT mice were lethally irradiated, transplantation of limited numbers of uPAR$^{-/-}$ bone marrow cells resulted in reduced survival, suggesting that uPAR deficiency of donor cells impaired homing and engraftment (FIG. 4, Panel i). However, this defect was not attributable to a difference in expression of $\beta_1$-integrins on BM MNCs (% $\alpha_5\beta_1^+$ cells: 6.9±0.3 for WT cells versus 6.1±0.3 for uPAR$^{-/-}$ cells; N=3; P=NS). Thus, uPAR is expressed on engrafting BM-derived stem cells, and determines homing and retention.

Figure 5:
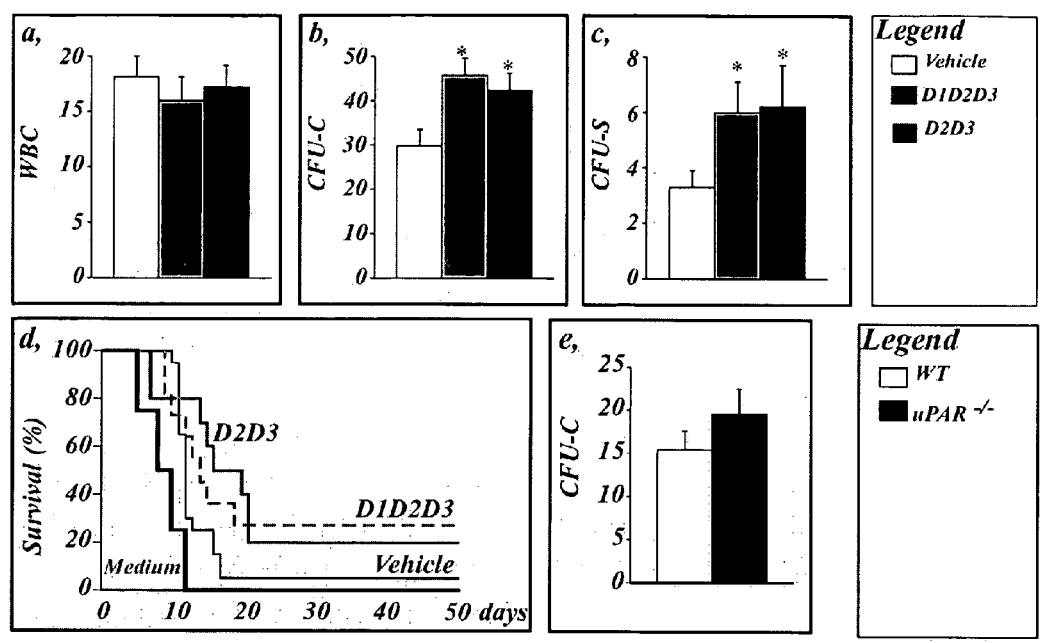
FIG. 5: Soluble uPAR stimulates stem/progenitor cell mobilization. Panels a-c, WT received daily s.c. injections of G-CSF in conjunction with i.p. injections of vehicle, 10 μg/day recombinant human $D_1D_2D_3$, or 10 μg/day $D_2D_3$ for five days, and circulating WBCs (Panel a), CFU-Cs (Panel b), and CFU-Ss (Panel c) were quantified. *: P<0.05 versus vehicle; N=10-11. PB MNCs from treated WT mice were transplanted into lethally irradiated syngeneic WT recipients, and survival was monitored (Panel d). As control group, lethally irradiated WT mice were injected with medium only. *: P<0.05 versus vehicle; N=10-20. Panel e, WT and uPAR$^{-/-}$ mice received a single i.v. bolus of 500 ng pertussis toxin, and after five days circulating CFU-Cs were quantified.

10. Soluble uPAR is a Chemokine, which Stimulates Stem/Progenitor Mobilization The uPA receptor (uPAR) is a membrane-bound glycoprotein containing three extracellular domains ($D_1D_2D_3$) and a glycosyl-phosphatidylinositol (GPI) anchor. As uPAR can be proteolytically cleaved by plasmin and other proteinases into soluble fragments of uPAR (suPAR), i.e., the $D_2D_3$ fragment and the $D_1D_2D_3$ fragment (Blasi et al. (2002). *Nat. Rev. Mol. Cell Biol.* 3:932-43; Andolfo et al. (2002), *Thromb. Haemost.* 88:298-306; Beaufort et al. (2004), *FEBS Lett.* 574:89-94), we also examined their role in stem cell mobilization. Using a home-made ELISA (Andolfo et al. (2002), *Thromb. Haemost.* 88:298-306), suPAR levels were detected in human BM plasma samples (28±3 ng/ml; N=4). In addition, suPAR appeared to function as a recruitment signal, since in vivo delivery of recombinant human suPAR (i.e., both $D_1D_2D_3$ as well as $D_2D_3$) enhanced G-CSF-mediated mobilization of HPCs and HSCs, but not WBCs by G-CSF in WT mice (FIG. 5, Panels a-d).

Although the role of the $D_1D_2D_3$ fragment in vivo remains unknown, the $D_2D_3$ fragment affects WBC motility either through chemotaxis via activation of G-protein coupled receptors (GPCRs), or through inhibition of $\beta$-integrin-mediated adhesion (Blasi et al. (2002), *Nat. Rev. Mol. Cell Biol.* 3:932-43; Resnati et al. (2002), *Proc. Natl. Acad. Sci. USA* 99:1359-64; Furlan et al. (2004), *J. Cell Sci.* 117:2909-16). In addition, $D_2D_3$-mediated chemotaxis appeared to be highly dependent on exposure of a chemotactic domain (consisting of the SRSRY sequence) at the cleavage site (Andolfo et al. (2002), *Thromb. Haemost.* 88:298-306; Resnati et al. (2002), *Proc. Natl. Acad. Sci. USA* 99:1359-64). However, the effect of suPAR on stem/progenitor mobilization was not attributable to its chemotactic properties. Indeed, the chemotactic $D_2D_3$ fragment failed to enhance migration of HPCs in vitro (HPCs in transwell: vehicle 460±176 after vehicle, N=3; 565±100 after $D_2D_3$, N=3; P=NS; 1363±323 after GM-CSF, N=5; P<0.05). Second, GPCR malfunctioning was not responsible for the impaired response in uPAR$^{-/-}$ mice, as administration of the GPCR antagonist pertussis toxin efficiently mobilized HPCs in uPAR$^{-/-}$ mice (FIG. 5, Panel e). Third, stem/progenitor cell mobilization was not only enhanced via administration of $D_2D_3$, but also by $D_1D_2D_3$ (FIG. 5, Panels a-d). We are analyzing suPAR levels in the BM during mobilization in mice, and we over-express the different fragments in vivo via adenoviral gene transfer with vector constructs for full-length $D_1D_2D_3$, $D_2D_3$ with ($D_2D_3$-288), and $D_2D_3$ without the chemotactic domain ($D_2D_3$-293). Thus, whereas uPAR is involved in HPC/HSC retention and its cleavage results in their mobilization, suPAR further amplifies stem/progenitor mobilization.

11. Loss of uPAR Reduces EPC Mobilization

As uPAR was expressed on engrafting hematopoietic stem/progenitor cells, we also investigated whether uPAR was expressed on EPCs and whether EPC mobilization was affected in uPAR$^{-/-}$ mice, as described in Example 7). Late-outgrowth EPC had abundant expression of uPAR (copies per copy $\beta$-actin: 44±17; N=3), and our data show that ischemia-driven mobilization of EPCs is significantly attenuated in ligated uPAR$^{-/-}$ mice.

12. Plasmin Activates MMPs During Mobilization

Figure 6:
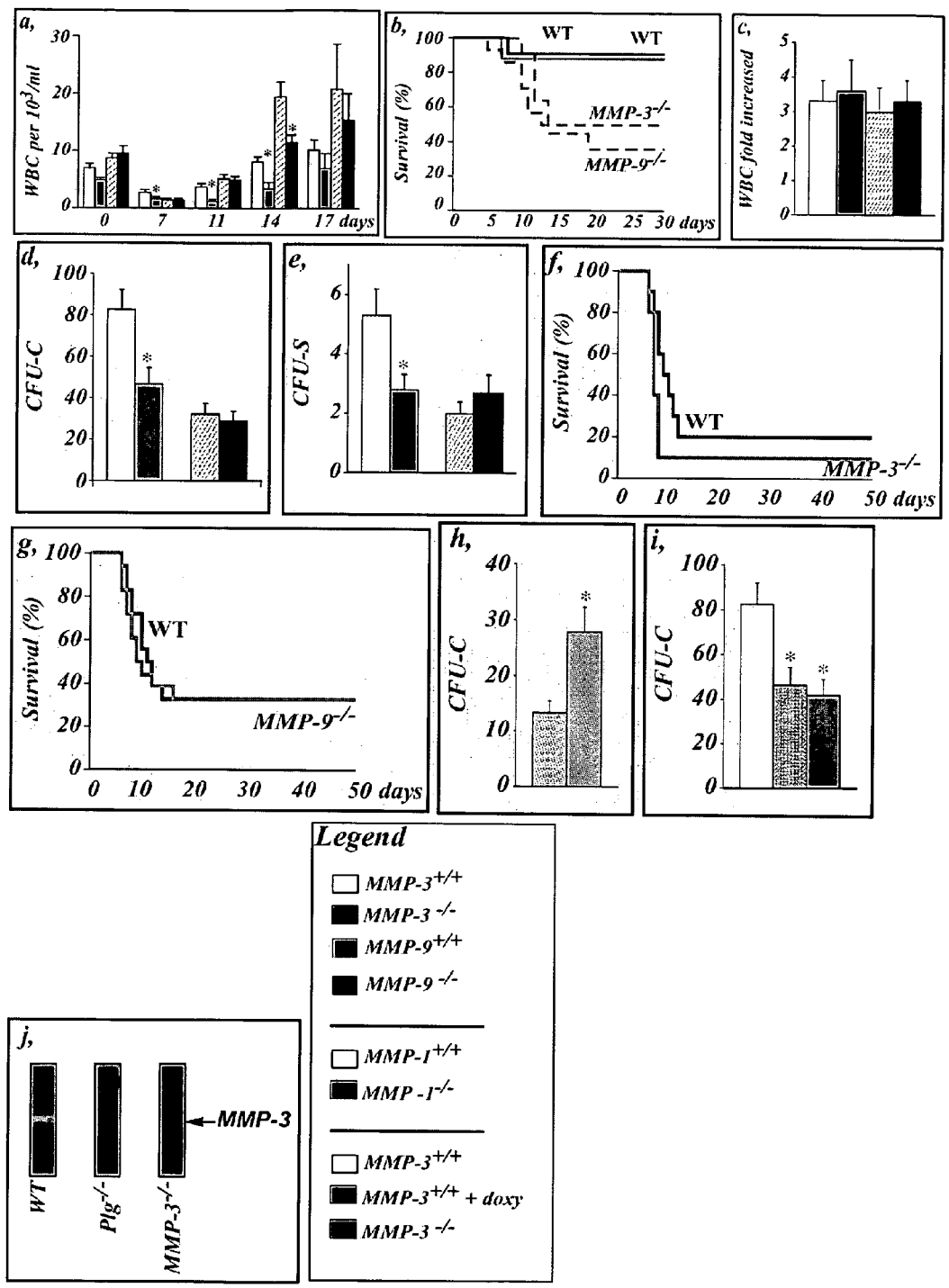
FIG. 6: Plasmin activates different MMPs during stem/progenitor cell mobilization. Panels a-b, MMP-3$^{+/+}$, MMP-3$^{-/-}$, MMP-9$^{+/+}$ and MMP-9$^{-/-}$ mice received a single i.v. bolus of 5-FU (250 and 200 mg/kg, respectively), and were followed up for WBCs (Panel a) and survival (Panel b). *: P<0.05 versus +/+; N=8-15. Panels c-g, MMP-3$^{+/+}$, MMP-3$^{-/-}$, MMP-9$^{+/+}$ and MMP-9$^{-/-}$ mice received daily s.c. injections of G-CSF for five days, and circulating WBCs (Panel c), CFU-Cs (Panel d), and CFU-Ss (Panel e) were quantified. *: P<0.05 versus +/+; N=8-13. PB MNCs of G-CSF-treated MMP-3$^{+/+}$ or MMP-3$^{-/-}$ were transplanted into lethally irradiated syngeneic MMP-3$^{+/+}$ recipients (Panel f), and PB MNCs of G-CSF-treated MMP-9$^{+/+}$ or MMP-9$^{-/-}$ mice were transplanted into lethally irradiated syngeneic MMP-9$^{+/+}$ recipients (Panel g), and survival was monitored. *: P<0.05 versus +/+; N=18-25. Panel h, TIMP-1$^{+/+}$ and TIMP-1$^{-/-}$ mice received daily s.c. injections of G-CSF for five days, and circulating CFU-Cs were quantified. *: P<0.05 versus +/+; N=8. Panel i, MMP-3$^{+/+}$ mice were treated with G-CSF and doxycycline or vehicle for five days, and circulating CFU-Cs were quantified. Note the similar reduction in MMP-3$^{-/-}$ mice. *: P<0.05 versus +/+; N=9-11. Panel j, plasmin activates MMPs during mobilization. Representative zymographies on bone marrow plasma samples of 5-FU-treated WT and Plg$^{-/-}$ mice for MMP-3 (Panel j). Samples of MMP-3$^{-/-}$ mice were used as negative control.
Figure 7:
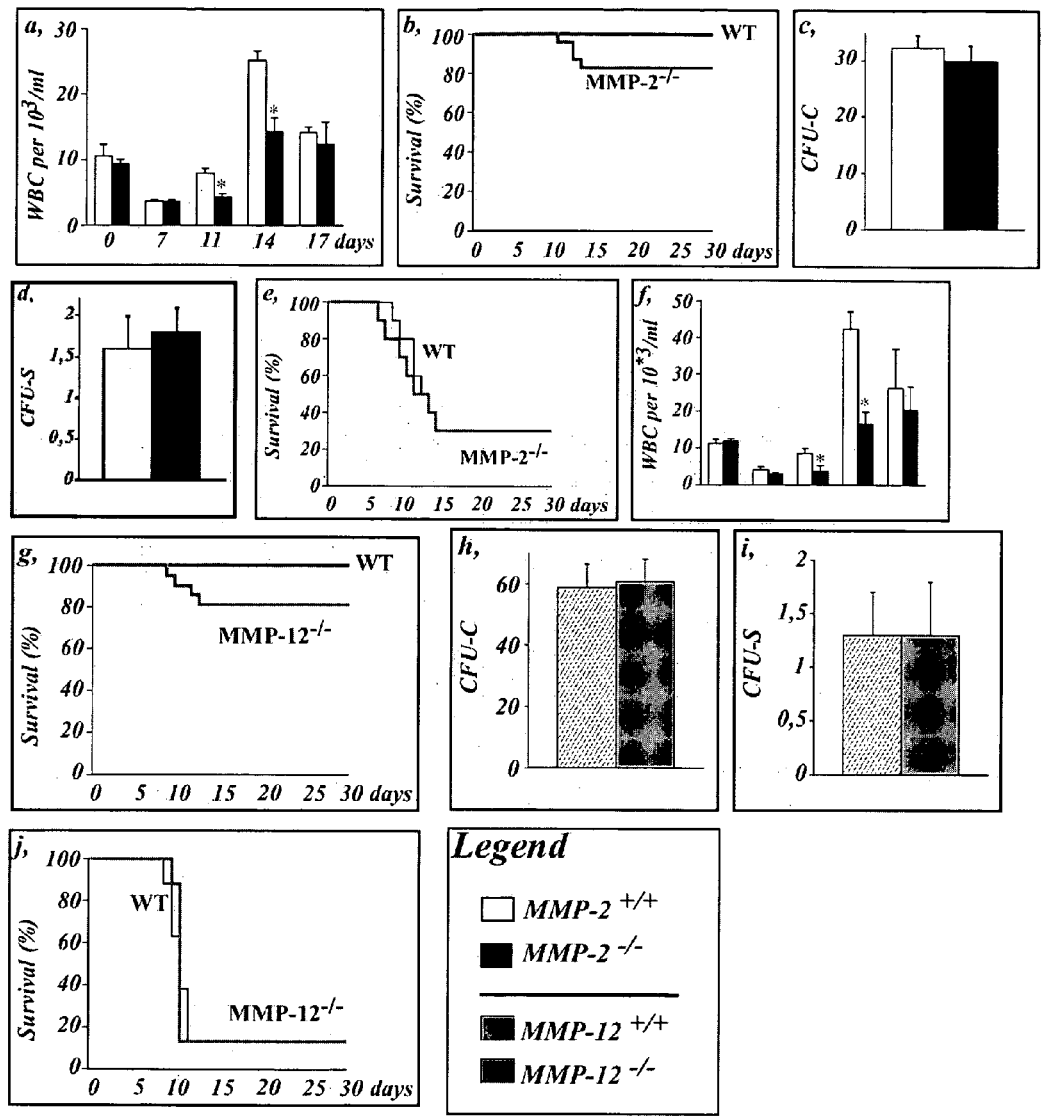
FIG. 7: Plasmin activates different MMPs during stem/progenitor cell mobilization. Panels a-b, MMP-2$^{+/+}$ and MMP-2$^{-/-}$ mice received a single i.v. bolus of 5-FU (200 mg/kg), and were followed up for WBCs (Panel a) and survival (Panel b). *: P<0.05 versus +/+; N=13-15. Panels c-e, MMP-2$^{+/+}$ and MMP-2$^{-/-}$ mice received daily s.c. injections of G-CSF for five days, and circulating CFU-Cs (Panel c), and CFU-Ss (Panel d) were quantified (N=10-13). PB MNCs of G-CSF-treated MMP-2$^{+/+}$ or MMP-2$^{-/-}$ were transplanted into lethally irradiated syngeneic MMP-2$^{+/+}$ recipients (Panel e), and survival was monitored (N=20). Panels f-g, MMP-12$^{+/+}$ and MMP-12$^{-/-}$ mice received a single i.v. bolus of 5-FU (200 mg/kg), and were followed up for WBCs (Panel j) and survival (Panel g). *: P<0.05 versus +/+; N=8-12. Panels h-j, MMP-12$^{+/+}$ and MMP-12$^{-/-}$ mice received daily s.c. injections of G-CSF for five days, and circulating CFU-Cs (Panel h), and CFU-Ss (Panel i) were quantified (N=10-11). PB MNCs of G-CSF-treated MMP-12$^{+/+}$ or MMP-12$^{-/-}$ were transplanted into lethally irradiated syngeneic MMP-2$^{+/+}$ recipients (Panel j), and survival was monitored (N=8).

We also investigated which possible downstream targets of plasmin during stem cell mobilization are involved. As plasmin is capable of activating the matrix metalloproteinases (MMPs) MMP-2, MMP-3, MMP-9 and MMP-12 (Heymans et al. (1999), *Nat. Med.* 5:1135-42) and since MMP-9 has been recently implicated in stem cell mobilization after 5-FU-induced myeloablation (Heissig et al. (2002), *Cell* 109:625-37), we analyzed which MMPs were involved in stem cell mobilization by phenotyping mice lacking MMP-2 (MMP-2$^{-/-}$), MMP-3 (MMP-3$^{-/-}$), MMP-9 (MMP-9$^{-/-}$) and MMP-12 (MMP-12$^{-/-}$). When the BM was ablated through 5-FU, deficiency of all these MMPs resulted in reduced survival and delayed hematopoietic recovery (FIG. 6, Panels a and b; FIG. 7, Panels a, b, f, g). Thus, MMP-2, MMP-3, MMP-9 and MMP-12 are required for 5-FU-induced mobilization and recovery. In contrast, when testing the response to G-CSF, mobilization of stem cell/progenitors was normal in MMP-2$^{-/-}$, MMP-9$^{-/-}$ and MMP-12$^{-/-}$ mice (FIG. 6, Panels c-e, g; FIG. 7, Panels c-e, h-j), indicating that these MMPs had a negligible role. In contrast, MMP-3 was involved in G-CSF-induced stem cell mobilization, as HSCs and HPCs, but not WBCs were reduced in MMP-3$^{-/-}$ mice by 44% and 47%, respectively (FIG. 6, Panels c-f). Deficiency of TIMP-1 (TIMP$^{-/-}$), the primary inhibitor of MMP-activity, significantly enhanced mobilization, whereas treatment of WT mice with the MMP-inhibitor doxycycline-impaired recruitment (FIG. 6, Panels h and i). Thus, MMPs appear to be differentially involved in stem cell recruitment after 5-FU-induced myeloablation or G-CSF.

We then investigated whether MMPs were activated by plasmin during stem cell mobilization. Zymography of BM plasma samples revealed that active MMP-2, -3 and -9 were undetectable in baseline conditions. At seven days after 5-FU-induced myeloablation, active MMP-2, MMP-3 and MMP-9 levels were elevated in the BM plasma of WT but were attenuated in Plg$^{-/-}$ mice (FIG. 6, Panel j). Thus, plasmin activates MMPs in the bone marrow during stem cell mobilization.

13. Plasmin Abrogates Stem/Progenitor Cell Retention in the BM Niche, Thereby Making them Permissive for Mobilization To become mobilized, stem and progenitor cells need to migrate through the BM extracellular matrix (ECM), which is rich in fibronectin in the osteoblastic zone, and in collagen IV and laminin in the vascular zone (Nilsson et al. (2002), *J. Histochem. Cytochem.* 46:371-7). These ECM proteins support retention and homing of stem cells in their niche and maintain the BM-blood barrier (Nilsson et al. (1998), *J. Histochem. Cytochem.* 46:371-7; Prosper et al. (1998), *J. Clin. Invest.* 101:2456-67) and can be degraded by plasmin (Liotta et al. (1981), *Cancer Res.* 41:4629-36). Immunostaining of BM sections from 5-FU-treated mice revealed increased immunoreactivity and a higher percentage of immuno-positive staining for fibronectin (fibronectin$^+$ area as % of total area: 14±2% in uPA$^{-/-}$ mice versus 9±1% in WT mice; N=3-4; P<0.05), collagen IV (collagen-IV$^+$ area as % of total area: 26±1% in uPA$^{-/-}$ mice versus 21±1% in WT mice; N=3-4; P<0.05) and laminin. In addition, immunoblotting on non-reduced BM plasma samples for fibronectin and laminin showed less dimeric/monomeric protein and more cleavage products in WT than in Plg$^{-/-}$ uPA$^{-/-}$ mice. Thus, plasmin efficiently degrades ECM components in the BM during mobilization.

In addition, quiescent stem/progenitor cells normally reside in BM niches because of molecular retention signals, such as membrane-bound Kit ligand (mKitL or KL). Hence, for their mobilization, mKitL/KL is proteolytically cleaved into a soluble form (sKitL; also called stem cell factor or SCF), which stimulates migration and proliferation (Heissig et al. (2002), *Cell* 109:625-37). Alternative splicing of the mKitL/KL gene results in tissue-specific expression of two isoforms (i.e., KL-1 and KL-2), of which KL-2 is prominently expressed in the BM (Tajima et al. (1998), *Proc. Natl. Acad. Sci. USA* 95:11903-8). As KL-2 contains a potential cleavage site for plasmin ($^{178}$Lys-Ala-Ala-Lys$^{181}$) (Majumdar et al. (1994), *J. Biol. Chem.* 269:1237-42), we investigated whether plasmin would also be involved in proteolytic cleavage of mKitL/KL into sKitL. Baseline levels of sKitL in BM plasma were comparable in WT, Plg$^{-/-}$, tPA$^{-/-}$ and uPA$^{-/-}$ mice. Although the sKitL levels in the BM plasma of WT mice were not increased after G-CSF, they were elevated 14-fold and 2.5-fold at seven and ten days after 5-FU treatment, respectively. In contrast, sKitL levels were significantly reduced in Plg$^{-/-}$ mice at seven days and in uPA$^{-/-}$ mice at ten days following 5-FU. Thus, generation of plasmin during mobilization results in cleavage of mKitL/KL into sKitL.

EXPERIMENTAL METHODS

Antibodies, ELISA, Reagentia, Protease Activity, and Western Blotting

BM extracellular fluid (BM plasma) from mice was obtained as described previously (Petit et al. (2002), *Nat. Immunol.* 3:687-94). BM plasma from healthy volunteers was obtained by using the first 10 ml of collection via puncture in the iliac crest under local anesthesia, and immediate anti-coagulation with EDTA. Protein extraction on BM cells was performed as described (Heymans et al. (1999), *Nat. Med.* 5:1135-42). Murine sKitL and SDF1α protein levels were quantified using commercial available ELISA (R&D Systems, Abingdon, UK). Murine plasminogen, and murine and human suPAR were quantified by home-made ELISA (Heymans et al. (1999), *Nat. Med.* 5:1135-42; Sier et al. (2004), *Thromb. Haemost.* 91:403-11). Lyophilized pertussis toxin was obtained from List Laboratories. MMP-2, MMP-9, and MMP-12 activities were measured using gelatin-zymography, uPA and MMP-3 activities were measured using casein-zymography, as described previously (Heymans et al. (1999), *Nat. Med.* 5:1135-42). Samples from gene-deficient mice were used as negative controls. Plasmin activity of BM plasma or cells (pericellular activity) was measured using substrate colorimetry (S2403), as described previously (Heymans et al. (1999), *Nat. Med.* 5:1135-42). Fibrinolytic activity was measured using a modified fluorescent-based in vitro clot lysis assay (Heymans et al. (1999), *Nat. Med.* 5:1135-42). Western blotting was performed on non-reduced samples, which were neutralized with a cocktail of protease inhibitors (Complete Inhibitor, Roche). ECM components/fragments were detected with antibodies against mouse fibronectin and laminin (Sigma), and human $D_1D_2D_3$ and $D_2D_3$ (Andolfo et al. (1999), *Thromb. Haemost.* 88:298-306), secondary HRP-labeled antibodies (DAKO), and ECL detection system (Amersham Pharmacia).

FACS Analysis

Murine BM cells were filtered through a 40 µm nylon mesh (Falcon) and stained with labeled anti-mouse antibodies against CD11b, Gr-1, CD3ε, CD19, Sca-1, $α_5β_1$, (BD Biosciences), cKit (eBioscience). Anti-mouse $α_4β_1$, antibodies were generated from hybridoma (PS/2; ATCC), and detected using a secondary labeled anti-rat antibody (Caltag). Mouse annexin II was detected using a goat anti-annexin II antibody (Santa Cruz), and a secondary labeled rabbit anti-goat antibody (Caltag). Mouse uPAR was detected using a rabbit anti-mouse uPAR antibody (Sier et al. (2004), *Thromb. Haemost.* 91:403-11), and a secondary labeled goat anti-rabbit antibody (BD Biosciences). Control stainings included matched isotype antibodies and pre-immune antibodies. Non-specific binding was prevented by addition of mouse serum (DAKO), as alternative for Fc-receptor block. For cell cycle analysis, BM cells were stained with Sca-1-FITC and treated with PI/RNAse (BD Biosciences), as previously described (Heissig et al. (2002), *Cell* 109:625-37). From EDTA-anti-coagulated human blood, full blood counts were performed, MNCs were prepared using Lymphoprep (Axis-Shield), counted, and 1×10$^6$ PB MNCs were stained with anti-human CD34 (Tebu Bio).

Immunohistochemistry

Mice were killed via cervical dislocation, femurs were removed, fixed in 2% paraformaldehyde in PBS for 24 hours, and decalcified in EDTA solution. After dehydration and paraffin embedding, 10 µm transverse sections were prepared on Superfrost Plus slides. Immunohistochemistry was performed using antibodies against VWF (DAKO), MMP-9 (Oncogene), tPA, uPA, MMP-2, MMP-3, MMP-12 (Santa Cruz), laminin, fibronectin (Sigma), and collagen IV (kind gift from A. Noel). Analysis was performed on a Zeiss Axioplan2, a 3CCD video camera (DXC-93OP, Sony), and KS300 software.

Animal Studies

Wild-type mice and mice lacking Plg, both tPA and uPA, tPA, uPA, uPAR, PAI-1, $α_2$AP, MMP-2 (kind gift from S. Itohara), MMP-3 (kind gift from J. Mudgett), MMP-9, MMP-12 (kind gift from S. Shapiro), and TIMP-1 (obtained by courtesy of P. Soloway) were used, and housed in barrier cages (individually ventilated) (Heymans et al. (1999), *Nat. Med.* 5:1135-42). Mice were injected with a bolus of 5-FU (200 or 250 mg/kg) i.v., or with G-CSF (200 µg/kg/d, Filgrastrim, Amgen) s.c. for five consecutive days. Peripheral blood was repetitively sampled by retro-orbital puncture under light anesthesia, and full blood counts (EDTA buffered) were determined on a hemocytometer (Abbott Cell Dyn 1300). Peripheral blood smears were stained using Giemsa-May-Grunwald and at least 200 cells were analyzed. Tranexamic acid (exacyl) was administered via osmotic minipumps (1.8 mg/d, Alzet 2001) and via drinking water (20 mg/ml) (Hattori et al. (2000), *J. Clin. Invest.* 106:1341-50). Doxycycline was administered via drinking water, protected from light (30 mg/kg) (Pyo et al. (2000), *J. Clin. Invest.* 105:1641-9). Pertussis toxin (500 ng, List Laboratories) diluted in saline was administered in i.v. bolus (Papayannopoulou et al. (2003), *Blood* 101:4739-47). Tenecteplase (metalyse, 100 mg/kg) or solvent was administered via daily intra-peritoneal injections. Microplasmin or vehicle (Thromb-X) was administered via osmotic minipumps (100 µg/day, Alzet 2001). Endotoxin levels were below 0.5 EU/mg protein. Human recombinant $D_1D_2D_3$ and $D_2D_3$ (both 10 µg/day i.p.) were produced in CHO cells, and purified using antibody columns (Andolfo et al. (1999), *Thromb. Haemost.* 88:298-306). Endotoxin levels were below 5 EU/mg protein. Adenoviral vectors were developed using Stratagene AdEasy, and 200 µl containing $1.3 \times 10^9$ plaque-forming units (pfu) were injected i.v. (Heymans et al. (1999), *Nat. Med.* 5:1135-42).

Stem/Progenitor Cell Assays and Transplantation Experiments

Mononuclear cells (MNCs) were prepared via Lympholiter-M (Cedarlane) and density centrifugation. For CFU-C assays, bone marrow cells ($5 \times 10^4$), or PB MNCs ($1 \times 10^5$ or $5 \times 10^5$) were plated in 35 mm dishes (Stem Cell Technologies) using methylcellulose supplemented with growth factors (MethoCult, Stem Cell Technologies), and colonies were blindly scored after seven and thirteen days, respectively, using an inverted microscope (Luttun et al. (2002), *Nat. Med.* 8:831-40). For inhibition of annexin II, bone marrow cells were pre-incubated for 45 minutes at 37° C. with 1 µg/ml of goat polyclonal anti-annexin II antibodies (Santa Cruz) (Han et al. (2004), *Acta. Pharmacol. Sin.* 25:602-10). For LTC-IC assays, AFT024 mouse bone marrow stromal cells ($1 \times 10^5$ cell/ml) were seeded in 0.1% gelatin-coated 12-well plates at 33° C. in Myelocult (Stem Cell Technologies) with $1 \times 10^{-6}$ M hydrocortisone (Sigma), overlaid with $1 \times 10^6$ bone marrow cells, and cultured with twice a week half change of medium (Nolta et al. (2002), *Leukemia* 16:352-61). After five weeks of culture, cells were trypsinized, counted, plated in MethoCult, and CFU-Cs were scored after nine days. For total bone marrow transplantation, lethal total body irradiation (9.5 Gy), and transplantation of $5 \times 10^6$ bone marrow cells were performed in syngeneic recipients, and mice were allowed to recover for at least six weeks (Heymans et al. (1999), *Nat. Med.* 5:1135-42). For CFU-S assays, lethal total body irradiation (9.0 to 9.5 Gy), and transplantation of mobilized PB MNCs (1 to $1.5 \times 10^5$) were performed in syngeneic recipients, survival was monitored or splenic colonies were blindly scored after twelve days using a dissection microscope. For bone marrow proliferation index, bone marrow cells from treated mice were plated in 96-well plates, CellTiter96 (Promega) was added, and repetitive colorimetric readings were performed at OD 490 nm. For chemotaxis assays, $1 \times 10^6$ freshly prepared BM MNCs were added to 0.25% gelatin-coated 8 µm-pore sized transwells (24-well, Costar) with vehicle, 100 ng/ml recombinant human GM-CSF (R&D systems) or $D_2D_3$ in the bottom well. After overnight incubation, the migrated non-adherent cells in the bottom wells were collected, counted, plated in MethoCult and CFU-Cs were scored after twelve days.

Homing Experiments

For adhesion assays, OP9 mouse stromal cells (ATCC, provided by C. Van Geet) were seeded at $8 \times 10^5$ cells/ml in 24-well plates, and overlaid with $1 \times 10^5$ freshly prepared BM MNCs, which were labeled with Vybrant CFDA SE Cell Tracer Kit (Molecular Probes). Labeling efficiency was >99%. For fibronectin adhesion assays, 24-well plates were coated >1 hour at room temperature with 10 µg/ml murine fibronectin (Invitrogen) in PBS. Kinetic experiments revealed that four hours of adhesion resulted in optimal evaluation of adhesion. Assays were terminated by gently washing twice with PBS, and cells were fixed with 2% paraformaldehyde (Sigma). Analysis was performed on five random fields per well at 20× magnification (Zeiss LSM 510) and quantified using KS300 software (Zeiss).

Bleeding Assays

In mice treated with vehicle or microplasmin, full blood counts were performed, and bleeding time was determined by tail clipping (2 mm). To evaluate rebleeding (i.e., secondary oozing from bleeding time wounds), the tail was immersed in prewarmed (37° C.) saline containing 14 mM tri-sodium citrate. After 60 minutes, RBC counts were determined to quantify blood loss (Suzuki et al. (2004), *J. Thromb. Haemost.* 2:1617-21). Activated partial thromboplastin time (aPTT), and plasma concentration of fibrinogen and $\alpha_2 AP$ were determined by standard laboratory techniques (Suzuki et al. (2004), *J. Thromb. Haemost.* 2:1617-21).

Statistics

In general, all data, represented as mean±SEM, were statistically analyzed by unpaired Student's t-test, using Instat3 software. Cumulative survival statistics were calculated by Kaplan-Meier statistics, using Statistica software. Patient data were compared using paired Student's t-test, using Instat3 software. $P < 0.05$ was considered statistically significant.

REFERENCES

1. Hattori K., et al., Vascular endothelial growth factor and angiopoietin-1 stimulate postnatal hematopoiesis by recruitment of vasculogenic and hematopoietic stem cells. *J. Exp. Med.*, 2001, 193(9):1005-14.
2. Hattori K., et al., Plasma elevation of stromal cell-derived factor-1 induces mobilization of mature and immature hematopoietic progenitor and stem cells. *Blood*, 2001, 97(11):3354-60.
3. Hattori K., et al., Placental growth factor reconstitutes hematopoiesis by recruiting VEGFR1(+) stem cells from bone-marrow microenvironment. *Nat. Med.*, 2002, 8(8): 841-9.
4. Asahara T., et al., VEGF contributes to postnatal neovascularization by mobilizing bone marrow-derived endothelial progenitor cells. *EMBO J.*, 1999, 18(14):3964-72.
5. Grant M. B., et al., Adult hematopoietic stem cells provide functional hemangioblast activity during retinal neovascularization. *Nat. Med.*, 2002, 8(6):607-12.
6. Orlic D., et al., Bone marrow cells regenerate infarcted myocardium. *Nature*, 2001, 410(6829):701-5.
7. Yamaguchi J., et al., Stromal Cell-Derived Factor-1 Effects on Ex Vivo Expanded Endothelial Progenitor Cell Recruitment for Ischemic Neovascularization. *Circ.* 2003, 107: 1316-22.

8. Takahashi T., et al., Ischemia- and cytokine-induced mobilization of bone marrow-derived endothelial progenitor cells for neovascularization. *Nat. Med.,* 1999, 5(4):434-8.
9. Orlic D., et al., Mobilized bone marrow cells repair the infarcted heart, improving function and survival. *Proc. Natl. Acad. Sci. USA,* 2001, 98(18):10344-9.
10. Carmeliet P., et al., Synergism between vascular endothelial growth factor and placental growth factor contributes to angiogenesis and plasma extravasation in pathological conditions. *Nat. Med.,* 2001, 7(5):575-83.
11. Abtahian F., et al., Regulation of blood and lymphatic vascular separation by signaling proteins SLP-76 and Syk. *Science,* 2003, 299(5604):247-51.
12. Luttun A., et al., Revascularization of ischemic tissues by PlGF treatment, and inhibition of tumor angiogenesis, arthritis and atherosclerosis by anti-Flt1. *Nat. Med.,* 2002, 8(8):831-40.
13. Heissig B., et al., Recruitment of stem and progenitor cells from the bone marrow niche requires MMP-9 mediated release of kit-ligand. *Cell,* 2002, 109(5):625-37.
14. Petit I., et al., G-CSF induces stem cell mobilization by decreasing bone marrow SDF-1 and up-regulating CXCR4. *Nat. Immunol.,* 2002, 3(7):687-94.
15. McWilliam N., et al., Plasminogen activator in acute myeloid leukaemic marrows: u-PA in contrast to t-PA in normal marrow. *Br. J. Haematol.,* 1998, 101(4):626-31.
16. Plesner T., N. Behrendt and M. Ploug, Structure, function and expression on blood and bone marrow cells of the urokinase-type plasminogen activator receptor, uPAR. *Stem Cells,* 1997, 15(6):398-408.
17. Carmeliet P., et al., Plasminogen activator inhibitor-1 gene-deficient mice. II. Effects on hemostasis, thrombosis, and thrombolysis. *J. Clin. Invest.,* 1993, 92(6):2756-60.
18. Dewerchin M., D. Collen and H. R. Lijnen, Enhanced fibrinolytic potential in mice with combined homozygous deficiency of alpha2-antiplasmin and PAI-1. *Thromb. Haemost.,* 2001, 86(2):640-6.
19. Collen D., Revival of plasmin as a therapeutic agent? *Thromb. Haemost.,* 2001, 86(3):731-2.
20. Nagai N., et al., Depletion of circulating alpha(2)-antiplasmin by intravenous plasmin or immunoneutralization reduces focal cerebral ischemic injury in the absence of arterial recanalization. *Blood,* 2001, 97(10):3086-92.
21. Luttun A., G. Carmeliet and P. Carmeliet, Vascular progenitors: from biology to treatment. *Trends Cardiovasc. Med.,* 2002, 12(2):88-96.
22. Majka S. M., et al., Distinct progenitor populations in skeletal muscle are bone marrow derived and exhibit different cell fates during vascular regeneration. *J. Clin. Invest.,* 2003, 111(1):71-9.
23. Priller J., et al., Targeting gene-modified hematopoietic cells to the central nervous system: use of green fluorescent protein uncovers microglial engraftment. *Nat. Med.,* 2001, 7(12):1356-61.
24. Nakatomi H., et al., Regeneration of hippocampal pyramidal neurons after ischemic brain injury by recruitment of endogenous neural progenitors. *Cell* 2002, 110(4):429-41.
25. LeCouter J., et al., Angiogenesis-independent endothelial protection of liver: role of VEGFR-1. *Science,* 2003, 299 (5608):890-3.
26. Otto W. R., Lung epithelial stem cells. *J. Pathol.,* 2002, 197(4):527-35.

What is claimed is:

1. A method for enhancing recruitment of stem cells and/or progenitor cells selected from the group consisting of bone marrow stem cells, bone marrow progenitor cells, and combinations thereof, said method comprising:

identifying a subject suffering from a disease or condition that would benefit from enhanced recruitment of stem cells and/or progenitor cells;

introducing to the subject a plasmin modulator, wherein the plasmin modulator is a plasmin activator selected from the group consisting of plasmin, plasminogen, chimeric plasminogen, tissue-type plasminogen activator, tenecteplase, urokinase-type plasminogen activator, alpha-enolase, staphylokinase, streptokinase, sulodexide, T-686 ((3E,4E)-3-benzylidene-4-(3,4,5-trimethoxy-benzylidene) pyrrolidine-2,5-dione), an antibody against plasminogen activator inhibitor, an antibody against alpha-2-antiplasmin, and microplasmin; and introducing to the subject a myelopoietic agent selected from the group consisting of G-CSF, M-CSF, IL-3, SCF, VEGF, VEGF-B, VEGF-C, VEGF-D, PlGF, PDGF-A, PDGF-C, PDGF-D, erythropoietin, and Flt3-ligand;

so as to enhance recruitment of the stem cells and/or progenitor cells.

2. The method according to claim 1, wherein said stem cells and/or progenitor cells comprise a hematopoietic cell.

3. The method according to claim 1, wherein said stem cells and/or progenitor cells comprise an endothelial progenitor cell.

4. The method according to claim 1, wherein the disease or condition is selected from the group consisting of ischemic diseases, lung injury, stroke, muscle degeneration, muscle dystrophy, liver injury, kidney injury, ischemic limb disease, ischemic heart disease, and acute myocardial infarction.

5. A method for enhancing recruitment of stem cells and/or progenitor cells used in patients, the method consisting of:

introducing a pharmaceutical composition to a patient having a disorder selected from the group consisting of: leukopenia or pancytopenia caused by chemotherapy, leukopenia or pancytopenia caused by bone marrow transplantation, congenital leukopenia, congenital neutropenia, idiopathic neutropenia, and AIDS, wherein the pharmaceutical composition comprises:

a plasmin activator selected from the group consisting of plasmin, plasminogen, chimeric plasminogen, tissue-type plasminogen activator, tenecteplase, alpha-enolase, staphylokinase, streptokinase, sulodexide, T-686 ((3E, 4E)-3-benzylidene-4-(3,4,5-trimethoxy-benzylidene) pyrrolidine-2,5-dione), an antibody against plasminogen activator inhibitor, an antibody against alpha-2-antiplasmin, and microplasmin; and a suitable pharmaceutical excipient, so as to enhance recruitment of stem cells and/or progenitor cells, thereby treating the patient.

6. The method according to claim 5, wherein said stem cell and/or progenitor cell comprises a hematopoietic cell.

7. The method according to claim 5, wherein said stem cell and/or progenitor cell comprises an endothelial progenitor cell.

8. A method for enhancing recruitment of stem cells and/or progenitor cells used in patients having a disorder selected from the group consisting of leukopenia or pancytopenia caused by chemotherapy, leukopenia or pancytopenia caused by bone marrow transplantation, congenital leukopenia, congenital neutropenia, idiopathic neutropenia, AIDS, and combinations of any thereof, the method comprising:

introducing a plasmin-modulator to stem cells and/or progenitor cells so as to enhance recruitment of bone marrow stem cells and/or bone marrow progenitor cells, wherein the plasmin modulator is a plasmin activator selected from the group consisting of plasmin, plasminogen, chimeric plasminogen, tissue-type plasminogen activator, tenecteplase, urokinase-type plasminogen activator, alpha-enolase, staphylokinase, streptokinase, sulodexide, T-686 ((3E,4E)-3-benzylidene-4-(3,4,5-trimethoxy-benzylidene) pyrrolidine-2,5-dione), an antibody against plasminogen activator inhibitor, an antibody against alpha-2-antiplasmin, and microplasmin; and introducing to said stem cells a myelopoietic agent selected from the group consisting of G-CSF, M-CSF, GM-CSF, IL-3, SCF, VEGF, VEGF-B, VEGF-C, VEGF-D, PlGF, PDGF-A, PDGF-C, PDGF-D, erythropoietin, and Flt3-ligand;

so as to enhance recruitment of stem cells and/or progenitor cells, thereby treating the disorder.

9. A method for enhancing recruitment of stem cells and/or progenitor cells used in patients having a disorder selected from the group consisting of leukopenia or pancytopenia caused by chemotherapy, leukopenia or pancytopenia caused by bone marrow transplantation, congenital leukopenia, congenital neutropenia, idiopathic neutropenia, AIDS, and combinations of any thereof, the method comprising:

introducing a plasmin-modulator to the stem cells and/or progenitor cells so as to enhance recruitment of bone marrow stem cells and/or bone marrow progenitor cells, wherein the plasmin-modulator is a plasmin activator selected from the group consisting of plasmin, plasminogen, chimeric plasminogen, tissue-type plasminogen activator, tenecteplase, alpha-enolase, staphylokinase, streptokinase, sulodexide, T-686 ((3E, 4E)-3-benzylidene-4-(3, 4, 5-trimethoxy-benzylidene) pyrrolidine-2, 5-dione), an antibody against plasminogen activator inhibitor, an antibody against alpha-2-antiplasmin, and microplasmin;

so as to enhance recruitment of stem cells and/or progenitor cells, thereby treating the patient.

10. The method according to claim 9, wherein said stem cell and/or progenitor cell comprises a hematopoietic cell.

11. The method according to claim 9, wherein said stem cell and/or progenitor cell comprises an endothelial progenitor cell.

* * * * *